United States Patent
Freddolino et al.

(10) Patent No.: US 12,246,056 B2
(45) Date of Patent: Mar. 11, 2025

(54) COMPOSITIONS AND METHODS FOR THE PRODUCTION OF CYSTEINE

(71) Applicant: The Regents of the University of Michigan, Ann Arbor, MI (US)

(72) Inventors: Lydia Petra Freddolino, Ann Arbor, MI (US); Mehdi Rahimpour, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 17/291,812

(22) PCT Filed: Nov. 6, 2019

(86) PCT No.: PCT/US2019/060086
§ 371 (c)(1),
(2) Date: May 6, 2021

(87) PCT Pub. No.: WO2020/097213
PCT Pub. Date: May 14, 2020

(65) Prior Publication Data
US 2021/0386818 A1    Dec. 16, 2021

Related U.S. Application Data

(60) Provisional application No. 62/756,635, filed on Nov. 7, 2018.

(51) Int. Cl.
| | | |
|---|---|---|
| *A61K 38/16* | (2006.01) | |
| *A01N 63/50* | (2020.01) | |
| *A01P 1/00* | (2006.01) | |
| *A61P 31/04* | (2006.01) | |
| *C07K 14/245* | (2006.01) | |
| *C12N 1/20* | (2006.01) | |

(52) U.S. Cl.
CPC ............ *A61K 38/164* (2013.01); *A01N 63/50* (2020.01); *A01P 1/00* (2021.08); *A61P 31/04* (2018.01); *C07K 14/245* (2013.01); *C12N 1/20* (2013.01)

(58) Field of Classification Search
None
See application file for complete search history.

(56) References Cited

U.S. PATENT DOCUMENTS

| | | | |
|---|---|---|---|
| 5,972,663 | A | 10/1999 | Winterhalter et al. |
| 6,218,168 | B1 | 4/2001 | Leinfelder et al. |
| 2004/0038352 | A1 | 2/2004 | Maier |
| 2009/0053778 | A1 | 2/2009 | Sauer et al. |
| 2009/0226984 | A1 | 9/2009 | Nonaka et al. |
| 2010/0028334 | A1 | 2/2010 | Cottarel et al. |

FOREIGN PATENT DOCUMENTS

| | | |
|---|---|---|
| CA | 2386539 A1 | 4/2001 |
| EP | 1571223 | 1/2010 |
| WO | WO 2016/025448 | 2/2016 |
| WO | WO 2017/176807 | 10/2017 |

OTHER PUBLICATIONS

Lee et al. ("Structure and Function of the *E. coli* Protein YmgB: a Protein Critical for Biofilm Formation and Acid-resistance," J Mol Biol. Oct. 12, 2007; 373(1): 11-26) (Year: 2007).*
International Search Report and Written Opinion for PCT/US19/60086. Mailed Jan. 24, 2020. 16 pages.
Awano et al., Effect of cysteine desulfhydrase gene disruption on L-cysteine overproduction in *Escherichia coli*. Appl Microbiol Biotechnol. Aug. 2003;62(2-3):239-43.
Awano et al., Identification and functional analysis of *Escherichia coli* cysteine desulfhydrases. Appl Environ Microbiol. Jul. 2005;71(7):4149-52.
Baba et al., Construction of *Escherichia coli* K-12 in-frame, single-gene knockout mutants: the Keio collection. Mol Syst Biol. 2006;2:2006. 0008. 1-7.
Bansal et al., Differential effects of epinephrine, norepinephrine, and indole on *Escherichia coli* O157:H7 chemotaxis, colonization, and gene expression. Infect Immun. Sep. 2007;75(9):4597-607.
Bergholz et al., Global transcriptional response of *Escherichia coli* O157:H7 to growth transitions in glucose minimal medium. BMC Microbiol. Oct. 29, 2007;7:97. 1-27.
Bourassa et al., Glycogen contributes to the environmental persistence and transmission of Vibrio cholerae. Mol Microbiol. Apr. 2009;72(1):124-38.
Chang et al., Carbon nutrition of *Escherichia coli* in the mouse intestine. Proc Natl Acad Sci U S A. May 11, 2004;101(19):7427-32.
Datsenko et al., One-step inactivation of chromosomal genes in *Escherichia coli* K-12 using PCR products. Proc Natl Acad Sci U S A. Jun. 6, 2000;97(12):6640-5.
Davies et al., A fatty acid messenger is responsible for inducing dispersion in microbial biofilms. J Bacteriol. Mar. 2009;191(5):1393-403.
Davis et al., Microscopic and physiologic evidence for biofilm-associated wound colonization in vivo. Wound Repair Regen. Jan.-Feb. 2008;16(1):23-9.
Deeley et al., Transcription initiation at the tryptophanase promoter of *Escherichia coli* K-12. J Bacteriol. Aug. 1982;151(2):942-51.
Desai et al., Antisense RNA strategies for metabolic engineering of Clostridium acetobutylicum. Appl Environ Microbiol. Mar. 1999;65(3):936-45.
Eydallin et al., Genome-wide screening of genes affecting glycogen metabolism in *Escherichia coli* K-12. FEBS Lett. Jun. 26, 2007;581(16):2947-53.

(Continued)

*Primary Examiner* — Christina Bradley
(74) *Attorney, Agent, or Firm* — Casimir Jones, S.C.; Tanya A. Arenson

(57) ABSTRACT

Provided herein are compositions and methods for generation of cysteine in microbial systems. Further provided herein are compositions and methods for reducing and eliminating biofilms.

6 Claims, 11 Drawing Sheets

Specification includes a Sequence Listing.

(56) References Cited

OTHER PUBLICATIONS

Eydallin et al., Genome-wide screening of genes whose enhanced expression affects glycogen accumulation in *Escherichia coli*. DNA Res. Apr. 2010;17(2):61-71.

Ferla et al., Bacterial methionine biosynthesis. Microbiology (Reading). Aug. 2014;160(Pt 8):1571-1584.

Frost et al., Mobile genetic elements: the agents of open source evolution. Nat Rev Microbiol. Sep. 2005;3(9):722-32.

Gaimster et al., Regulation of Indole Signalling during the Transition of *E. coli* from Exponential to Stationary Phase. PLoS One. Sep. 2, 2015;10(9):e0136691. 1-11.

Garges, S. A Short Course in Bacterial Genetics. A Laboratory Manual and Handbook for Escherichia coli and Related Bacteria. By Jeffrey H. Miller. Cold Spring Harbor Laboratory, Cold Spring Harbor, New York, 1992. Anal. Biochem. 1993; 210(1): 217.

Gogarten et al., Horizontal gene transfer, genome innovation and evolution. Nat Rev Microbiol. Sep. 2005;3(9):679-87.

Green et al., Genetic manipulation of acid formation pathways by gene inactivation in Clostridium acetobutylicum ATCC 824. Microbiology (Reading). Aug. 1996;142 ( Pt 8):2079-86.

Heap et al., The ClosTron: a universal gene knock-out system for the genus Clostridium. J Microbiol Methods. Sep. 2007;70(3):452-64.

Hirakawa et al., Indole induces the expression of multidrug exporter genes in *Escherichia coli*. Mol Microbiol. Feb. 2005;55(4):1113-26.

Imamura et al., Fusarium and Candida albicans biofilms on soft contact lenses: model development, influence of lens type, and susceptibility to lens care solutions. Antimicrob Agents Chemother. Jan. 2008;52(1):171-82.

Jones et al., Glycogen and maltose utilization by *Escherichia coli* O157:H7 in the mouse intestine. Infect Immun. Jun. 2008;76(6):2531-40.

Kaplan et al., Enzymatic detachment of Staphylococcus epidermidis biofilms. Antimicrob Agents Chemother. Jul. 2004;48(7):2633-6.

Lee et al., Bacterial charity work leads to population-wide resistance. Nature. Sep. 2, 2010;467(7311):82-5.

Lee et al., Indole cell signaling occurs primarily at low temperatures in *Escherichia coli*. ISME J. Oct. 2008;2(10):1007-23.

Lee et al., Indole is an inter-species biofilm signal mediated by SdiA. BMC Microbiol. May 18, 2007;7:42. 1-15.

Lee et al., Structure and function of the *Escherichia coli* protein YmgB: a protein critical for biofilm formation and acid-resistance. J Mol Biol. Oct. 12, 2007;373(1):11-26.

Lewis., Riddle of biofilm resistance. Antimicrob Agents Chemother. Apr. 2001;45(4):999-1007.

Li et al., A cAMP-independent carbohydrate-driven mechanism inhibits tnaA expression and TnaA enzyme activity in *Escherichia coli*. Microbiology (Reading). Sep. 2014;160(Pt 9):2079-2088.

Li et al., Indole production by the tryptophanase TnaA in *Escherichia coli* is determined by the amount of exogenous tryptophan. Microbiology (Reading). Feb. 2013;159(Pt 2):402-410.

McMeechan et al., Glycogen production by different *Salmonella enterica* serotypes: contribution of functional glgC to virulence, intestinal colonization and environmental survival. Microbiology (Reading). Dec. 2005;151(Pt 12):3969-3977.

Montero et al., *Escherichia coli* glycogen metabolism is controlled by the PhoP-PhoQ regulatory system at submillimolar environmental Mg2+ concentrations, and is highly interconnected with a wide variety of cellular processes. Biochem J. Oct. 23, 2009;424(1):129-41.

Mundhada et al., Engineering of high yield production of L-serine in *Escherichia coli*. Biotechnol Bioeng. Apr. 2016;113(4):807-16.

Newton et al., Properties of Crystalline Tryptophanase. J Biol Chem. Mar. 1965;240:1211-8.

O'Brien et al., Effects of Clostridium perfringens alpha-toxin (PLC) and perfringolysin O (PFO) on cytotoxicity to macrophages, on escape from the phagosomes of macrophages, and on persistence of C. perfringens in host tissues. Infect Immun. Sep. 2004;72(9):5204-15.

Omenn et al., Proteogenomics: Computational and Bioinformatics Innovations for Facilitating Identification of "Missing Proteins" and Predicting Functions of Unannotated Proteins (and Genes). Jul. 10, 2018. Institute for Advanced Studies, City University of Hong Kong Workshop on Genomics, Cells, & Matchematics. Retrieved on Jan. 6, 2020. <https://cityu-ias-www-upload.s3.amazonaws.com/eventpowerpoint/src/02-1%20-%20Prof.%20Gilbert%20OMENN_cb03ffa4-abc4-4cf2-93d0-12733d90b2d1.pdf> . 55 pages.

Parsek et al., Bacterial biofilms: an emerging link to disease pathogenesis. Annu Rev Microbiol. 2003;57:677-701.

Patten et al., Microarray analysis of RpoS-mediated gene expression in *Escherichia coli* K-12. Mol Genet Genomics. Dec. 2004;272(5):580-91.

Peano et al., Characterization of the *Escherichia coli* σ(S) core regulon by Chromatin Immunoprecipitation-sequencing (ChIP-seq) analysis. Sci Rep. May 28, 2015;5:10469. 1-15.

Petrova et al., Sticky situations: key components that control bacterial surface attachment. J Bacteriol. May 2012;194(10):2413-25.

Pizer et al., The Pathway and Control of Serine Biosynthesis in *Escherichia Coli*. J Biol Chem. Dec. 1963;238:3934-44.

Pye et al., The structure and mechanism of serine acetyltransferase from *Escherichia coli*. J Biol Chem. Sep. 24, 2004;279(39):40729-36.

Raboni et al., Tryptophan synthase: a mine for enzymologists. Cell Mol Life Sci. Jul. 2009;66(14):2391-403.

Rahimpour et al., GlgS, described previously as a glycogen synthesis control protein, negatively regulates motility and biofilm formation in *Escherichia coli*. Biochem J. Jun. 15, 2013;452(3):559-73.

Rahman et al., Effect of rpoS gene knockout on the metabolism of *Escherichia coli* during exponential growth phase and early stationary phase based on gene expressions, enzyme activities and intracellular metabolite concentrations. Biotechnol Bioeng. Jun. 20, 2006;94(3):585-95.

Roy et al., Cofactor: an accurate comparative algorithm for structure-based protein function annotation. Nucleic Acids Res. Jul. 2012;40(Web Server issue):W471-7.

Saito et al., Molecular cloning and characterization of a plant serine acetyltransferase playing a regulatory role in cysteine biosynthesis from watermelon. J Biol Chem. Jul. 7, 1995;270(27):16321-6.

Sambou et al., Capsular glucan and intracellular glycogen of *Mycobacterium tuberculosis*: biosynthesis and impact on the persistence in mice. Mol Microbiol. Nov. 2008;70(3):762-74.

Sievers et al., Fast, scalable generation of high-quality protein multiple sequence alignments using Clustal Omega. Mol Syst Biol. Oct. 11, 2011;7:539. 1-6.

Singh et al., CysK Plays a Role in Biofilm Formation and Colonization by Vibrio fischeri. Appl Environ Microbiol. Aug. 2015;81(15):5223-34.

Smets et al., Horizontal gene transfer: perspectives at a crossroads of scientific disciplines. Nat Rev Microbiol. Sep. 2005;3(9):675-8.

Snell. Tryptophanase: structure, catalytic activities, and mechanism of action. Adv Enzymol Relat Areas Mol Biol. 1975;42:287-333.

Sorensen et al., Studying plasmid horizontal transfer in situ: a critical review. Nat Rev Microbiol. Sep. 2005;3(9):700-10.

Stoodley et al., Biofilms as complex differentiated communities. Annu Rev Microbiol. 2002;56:187-209.

Stouthamer. A theoretical study on the amount of ATP required for synthesis of microbial cell material. Antonie Van Leeuwenhoek. 1973;39(3):545-65.

Thomas et al., Mechanisms of, and barriers to, horizontal gene transfer between bacteria. Nat Rev Microbiol. Sep. 2005;3(9):711-21.

Traxler et al., The global, ppGpp-mediated stringent response to amino acid starvation in *Escherichia coli*. Mol Microbiol. Jun. 2008;68(5):1128-48.

Tummala et al., Design of antisense RNA constructs for downregulation of the acetone formation pathway of Clostridium acetobutylicum. J Bacteriol. Mar. 2003;185(6):1923-34.

Wang et al., Glycogen with short average chain length enhances bacterial durability. Naturwissenschaften. Sep. 2011;98(9):719-29.

(56) References Cited

OTHER PUBLICATIONS

Whitchurch et al., Extracellular DNA required for bacterial biofilm formation. Science. Feb. 22, 2002;295(5559):1487.
Xavier et al., Biofilm-control strategies based on enzymic disruption of the extracellular polymeric substance matrix—a modelling study. Microbiology (Reading). Dec. 2005;151(Pt 12):3817-3832.
Yamamotoya et al., Glycogen is the primary source of glucose during the lag phase of *E. coli* proliferation. Biochim Biophys Acta. Dec. 2012;1824(12):1442-8.
Zhang et al., Cofactor: improved protein function prediction by combining structure, sequence and protein-protein interaction information. Nucleic Acids Res. Jul. 3, 2017;45(W1):W291-W299.

* cited by examiner

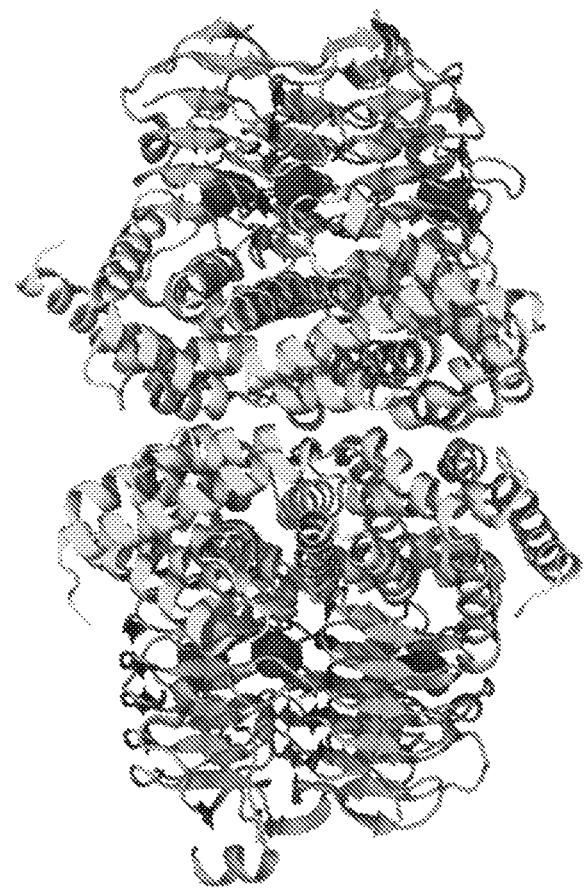
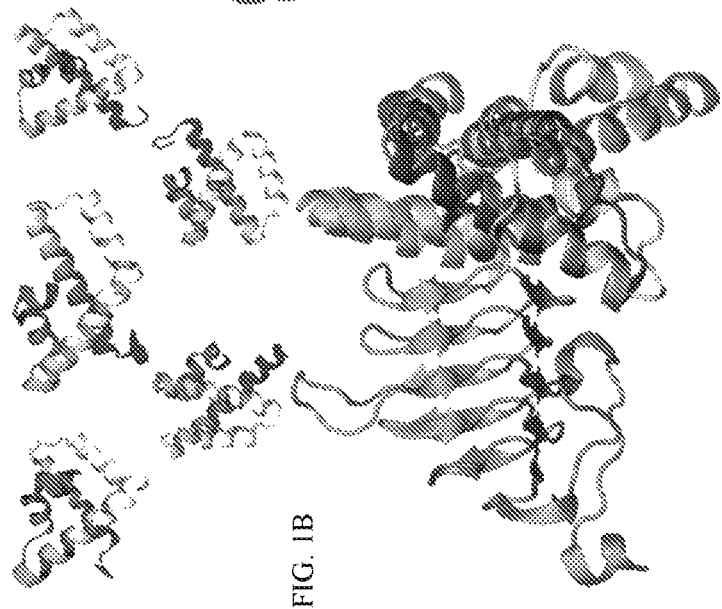
FIG. 1A
FIG. 1B
FIG. 1C

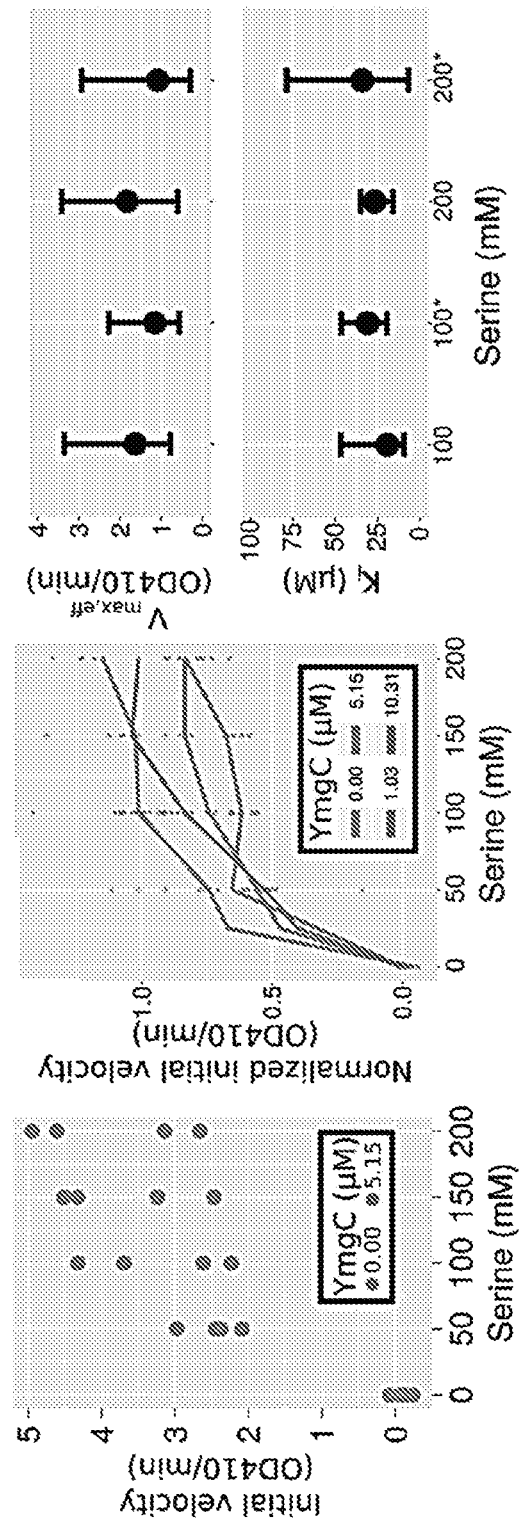

FIG. 3
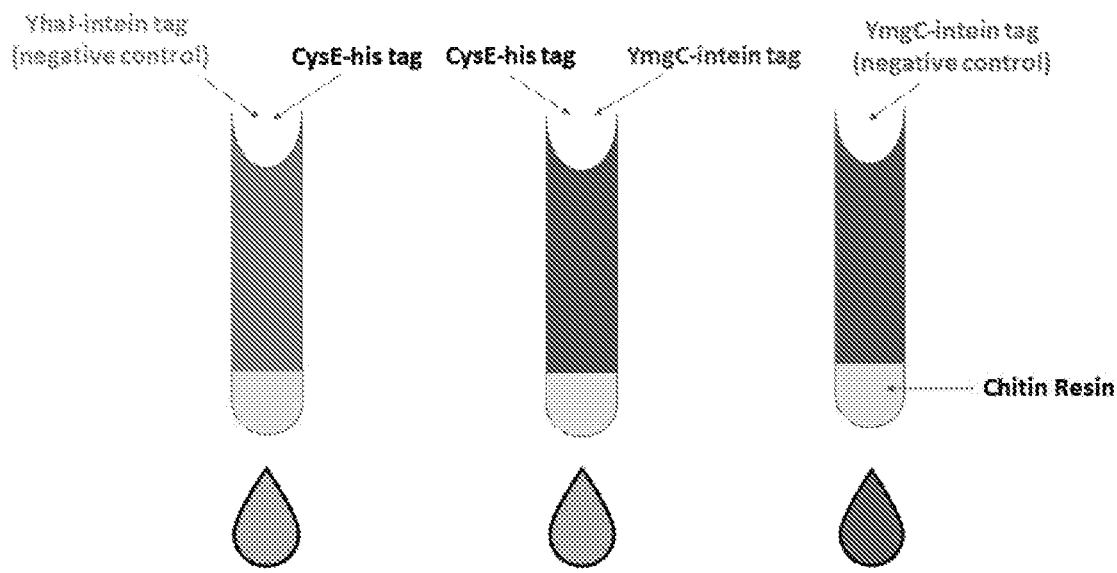
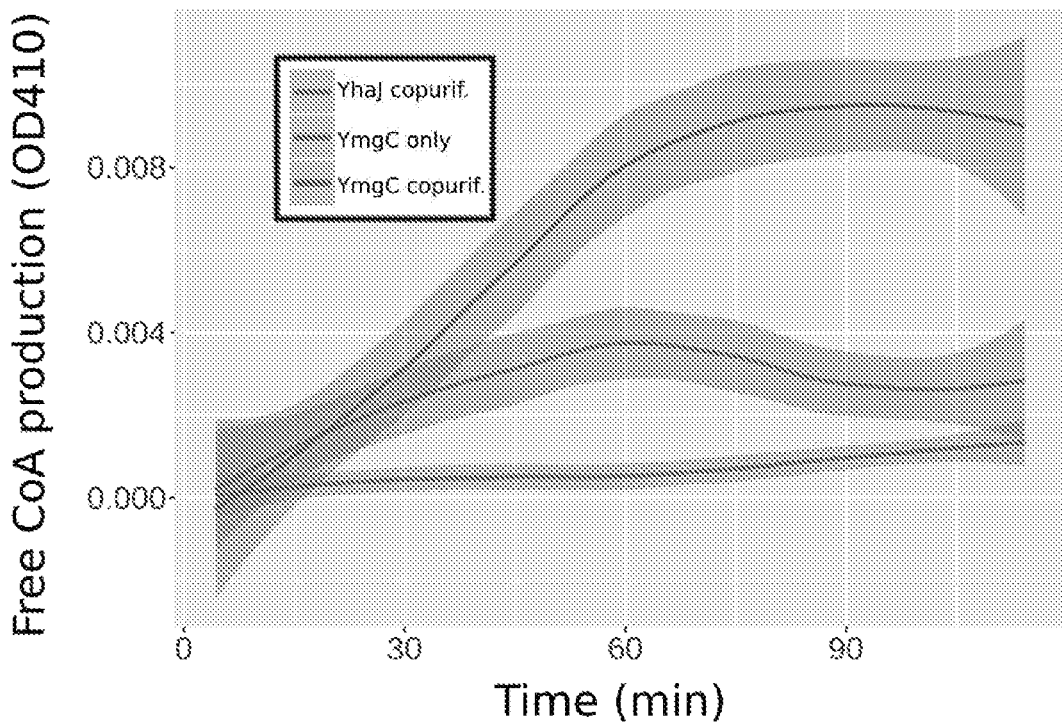

FIG. 9A
FIG. 9B
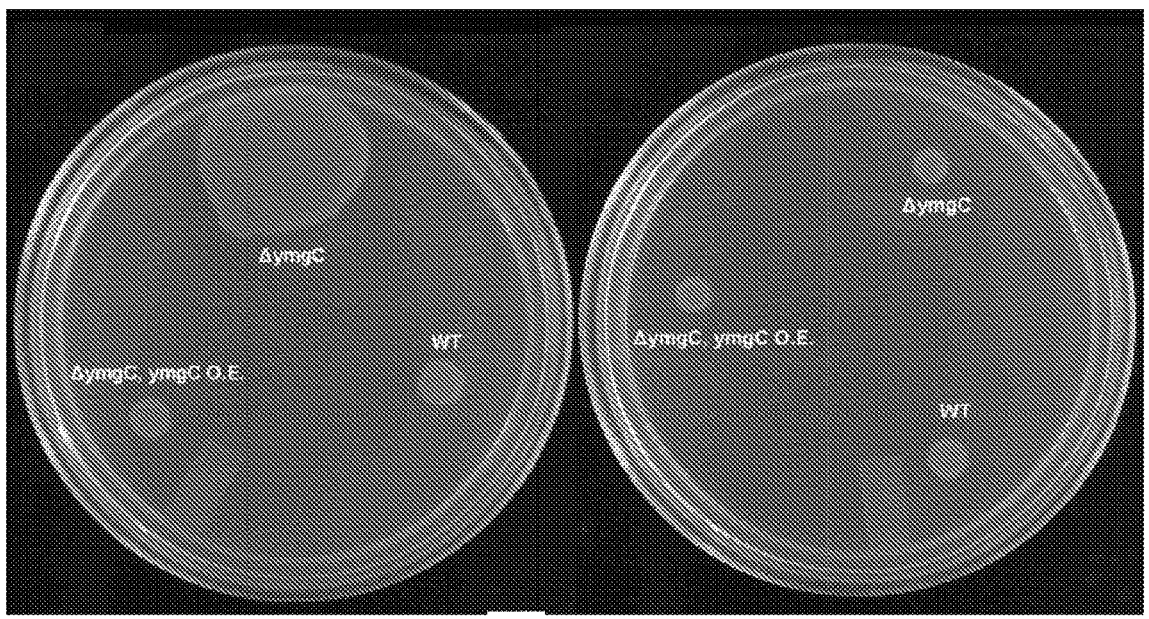
FIG. 9C
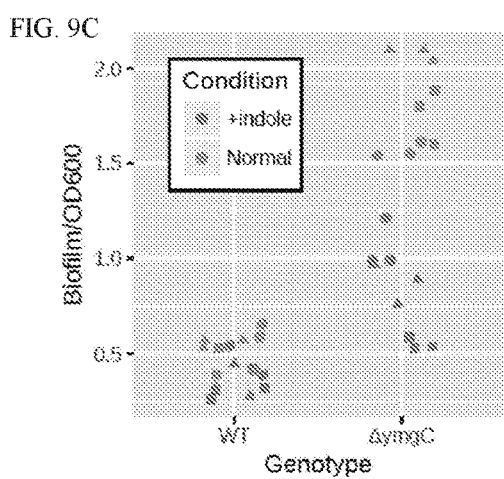
FIG. 9D
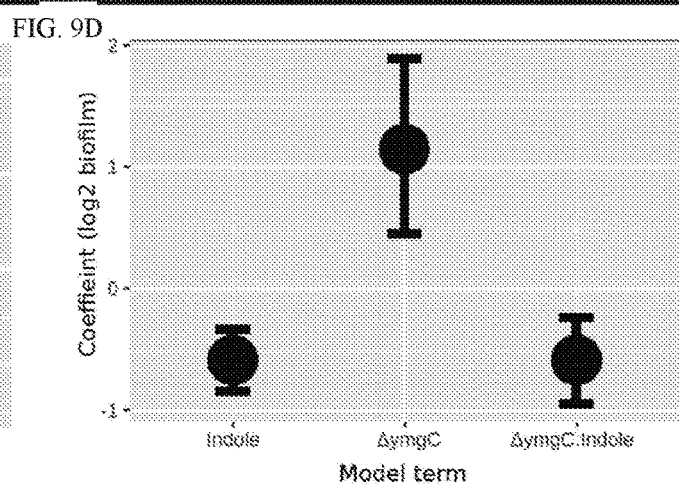

COMPOSITIONS AND METHODS FOR THE PRODUCTION OF CYSTEINE

STATEMENT OF RELATED APPLICATIONS

This is a national phase application under 35 U.S.C. § 371 of PCT International Application No. PCT/US2019/060086, filed Nov. 6, 2019, which claims the benefit of U.S. provisional patent application Ser. No. 62/756,635, filed Nov. 7, 2018, which is incorporated herein by reference in its entirety.

STATEMENT OF GOVERNMENT SUPPORT

This invention was made with government support under GM097033 awarded by the National Institutes of Health. The government has certain rights in the invention.

SEQUENCE LISTING

The text of the computer readable sequence listing filed herewith, titled "2024-12-16_35604.252_SQL_ST25", created Dec. 16, 2024, having a file size of 1,178 bytes, is hereby incorporated by reference in its entirety.

FIELD

Provided herein are compositions and methods for generation of cysteine in microbial systems. Further provided herein are compositions and methods for reducing and eliminating biofilms.

BACKGROUND

Cysteine is known to play a large role in both primary and second metabolism in most organisms. Many foods contain cysteine and can help supplement the cysteine that is made throughout the body. Outside of its functions in metabolism, cysteine is also used for other purposes such as animal feed, as a bread improver, in cosmetics, and in antidotes.

There are three main modes of industrial production of cysteine: keratin hydrolysate extraction of cysteine from animal and human sources such as feather, hair, and hooves; enzymatic bioconversion; and fermentation. The demand for non-animal origins of cysteine are growing so they can be utilized for vegetarian purposes. However, fermentation requires manipulation to produce more L-serine, the precursor for cysteine.

Improved methods for generating cysteine using fermentation methods are needed.

SUMMARY

Provided herein are compositions and methods for generation of cysteine in microbial systems. Further provided herein are compositions and methods for reducing and eliminating biofilms.

For example, in some embodiments, provided herein are bacteria lacking a functional ymgC gene. In some embodiments, the ymgC gene is deleted, mutated, or knocked out. In some embodiments, the bacteria are *E. coli*. In some embodiments, the bacteria produce increased levels of cysteine relative to bacteria with a functional ymgC gene. In some embodiments, the bacteria further comprise inactivation of one or more genes that encode polypeptides that degrade cysteine. In some embodiments, strains are modified to lack a functional poxB, glgC, ymgC, tnaA, pgaC, yaiP, ugD, ptA, ldhA, ashe, and/or pflB gene. In some embodiments, strains are modified to overexpress metH and/or yjeH.

Additional embodiments provide a kit or system, comprising: the bacteria described herein; and a culture medium. In some embodiments, the culture medium comprises one or more components selected from, for example, a carbon source and a sulfur source.

Yet other embodiments provide a method of killing or inhibiting growth of bacteria in a biofilm, comprising: contacting bacteria in a biofilm with a composition comprising a ymgC polypeptide, wherein the contacting kills or inhibits the growth of said bacteria. In some embodiments, the biofilm is on a surface of an object (e.g., a medical device) or in or on a subject. In some embodiments, the biofilm is in a wound. In some embodiments, the ymgC polypeptide is formulated as a pharmaceutical composition, a disinfecting, a cleaning solution, or is on a wound dressing.

Still other embodiments provide a composition, comprising: a ymgC polypeptide and a carrier. In some embodiments, the ymgC polypeptide is a fragment, variant, mimetic, etc. (e.g., that maintains the activity of full-length ymgC). In some embodiments, the carrier is a pharmaceutically acceptable carrier. In some embodiments, the carrier is an emulsion, lotion, cream, or gel.

Certain embodiments provide the use of a composition, comprising: a ymgC polypeptide in killing or inhibiting growth of bacteria in a biofilm.

Additional embodiments are described herein.

DESCRIPTION OF THE FIGURES

FIG. 1A through FIG. 1C shows YmgC models and alignment to serine acetyltransferase. (FIG. 1A) Top 5 QUARK ab initio models of *E. coli* YmgC, in order of decreasing confidence score from left to right. (FIG. 1B) Alignment of the best QUARK model with the serine acetyltransferase of *Y. pestis* (PDB code 3GVD). (FIG. 1C) Hexameric structure of *Y. pestis* SAT as defined in PDB 3GVD.

FIG. 2A through FIG. 2C shows in vitro kinetics of inhibition of CysE with YmgC. (FIG. 2A) Initial reaction rate of a standardized amount of purified CysE (0.3 µM) and acetyl-CoA (0.01 mM) either in the absence or presence of a five-fold excess (by mass) of purified YmgC. (FIG. 2B) Standardized reaction rates (rescaled so that the average reaction rate at 100 mM serine for each biological replicate was 1.0), at each of twenty combinations of substrate (serine) and inhibitor (YmgC) concentrations. (FIG. 2C) Fitted values and confidence intervals for the V max, eff and K i parameters for CysE acting under the inhibition of YmgC, fitted to equation 1 at fixed concentrations of either 100 mM or 200 mM serine.

FIG. 3 shows physical interaction between YmgC and CysE.

(FIG. 4A) Observed data (points) and posterior distributions (violin plots) for the ratio of biofilm levels observed for the noted cysE and ymgC genotypes to that of WT cells. (FIG. 4B) As in panel a, comparing data on tnaA and ymgC deletions.

(FIG. 5A) Glycogen level per unit protein at the onset of stationary phase, for cells of the stated genotype. (FIG. 5B) Growth curves (measured via optical density at 600 nm) for cells of the indicated genotypes growing in LB media.

(FIG. 6A) During exponential growth, the absence of YmgC and presence of CysE permits the flux of available serine to be used for cysteine and methionine biosynthesis. (FIG. 6B) At the onset of stationary phase, expression of YmgC rapidly inhibits CysE and shunts serine to tryptophan and (eventually) indole production, triggering the expression of genes related to stationary phase and long term survival, and inhibiting other energy-intensive processes.

(FIG. 8A) OD600-normalized biofilm formation for *S. typhimurium* LT2 (LT2), or the same strain with either the ASKA plasmid for ymgC (LT2+PymgC) or empty vector (LT2+Pempty). (FIG. 8B) Posterior 95% credible intervals for the ratio of biofilm formation in the plasmid containing strains relative to wild type LT2.

FIG. 9A through FIG. 9D shows supplementation with indole suppresses the effects of ymgC deletion. LB-based motility plates are shown for cells with the specified genotypes either in the absence (FIG. 9A) or presence (FIG. 9B) of 1 mM indole. (FIG. 9C) Biofilm formation of *E. coli* grown in LB in either the presence or absence of supplementation with 1 mM indole; different biological replicates are shown as different shapes. (FIG. 9D) Fitted coefficients and 95% credible intervals for a Bayesian multilevel model fitting the log 2 biofilm content (data from FIG. 9C) as a linear function of genotype, presence of indole, and an interaction term between genotype and indole (a random effect term was included that differed for each biological replicate).

DEFINITIONS

Figure 4A:
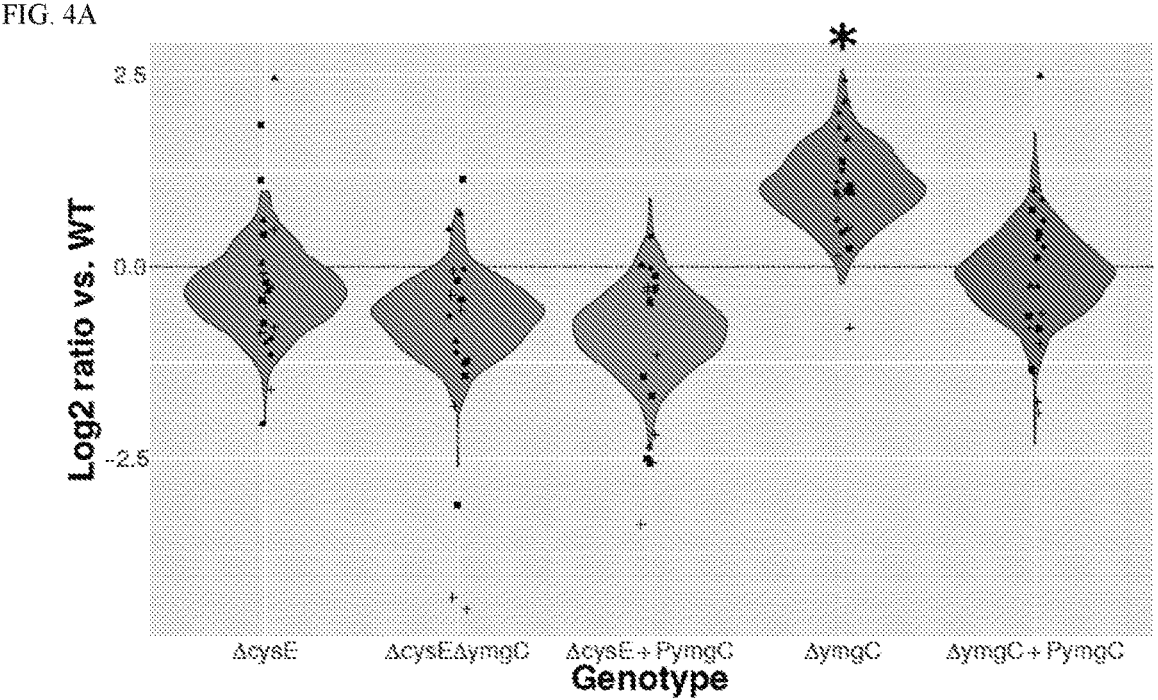
FIG. 4A through FIG. 4B shows biofilm formation and epistasis for YmgC interacting with CysE and TnaA.

To facilitate an understanding of the present disclosure, a number of terms and phrases are defined below:

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "microbe" refers to a microorganism and is intended to encompass both an individual organism, or a preparation comprising any number of the organisms.

As used herein, the term "microorganism" refers to any species or type of microorganism, including but not limited to, bacteria, archaea, fungi, protozoans, mycoplasma, and parasitic organisms.

As used herein, the term "fungi" is used in reference to eukaryotic organisms such as the molds and yeasts, including dimorphic fungi.

As used herein, the term "prokaryotes" refers to a group of organisms that usually lack a cell nucleus or any other membrane-bound organelles. In some embodiments, prokaryotes are bacteria. The term "prokaryote" includes both archaea and eubacteria.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "cell culture" refers to any in vitro culture of cells, including, e.g., prokaryotic cells and eukaryotic cells. Included within this term are continuous cell lines (e.g., with an immortal phenotype), primary cell cultures, transformed cell lines, finite cell lines (e.g., non-transformed cells), bacterial cultures in or on solid or liquid media, and any other cell population maintained in vitro.

As used herein the term "biofilm" refers to any three-dimensional, (e.g., matrix-encased) microbial community displaying multicellular characteristics. Accordingly, as used herein, the term biofilm includes surface-associated biofilms as well as biofilms in suspension, such as flocs and granules. Biofilms may comprise a single microbial species or may be mixed species complexes, and may include bacteria as well as fungi, algae, protozoa, or other microorganisms.

As used herein, the term "effective amount" refers to the amount of a composition (e.g., a composition comprising a ymgC polypeptide) sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., compositions comprising a ymgC polypeptide) to a physiological system (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.), topical administration and the like.

As used herein, the term "treating a surface" refers to the act of exposing a surface to one or more compositions comprising a ymgC polypeptide. Methods of treating a surface include, but are not limited to, spraying, misting, submerging, and coating.

As used herein, the term "co-administration" refers to the administration of at least two agent(s) (e.g., a ymgC polypeptide in combination with an antibiotic) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "wound" refers broadly to injuries to tissue including the skin, subcutaneous tissue, muscle, bone, and other structures initiated in different ways, for example, surgery, (e.g., open post cancer resection wounds, including but not limited to, removal of melanoma and breast cancer etc.), contained post-operative surgical wounds, pressure sores (e.g., from extended bed rest) and wounds induced by trauma. As used herein, the term "wound" is used without limitation to the cause of the wound, be it a physical cause such as bodily positioning as in bed sores or impact as with trauma or a biological cause such as disease process, aging process, obstetric process, or any other manner of biological process. Wounds caused by pressure may also be classified into one of four grades depending on the depth of the wound: i) Grade I: wounds limited to the epidermis; ii) Grade II: wounds extending into the dermis; iii) Grade III: wounds extending into the subcutaneous tissue; and iv) Grade IV: wounds wherein bones are exposed (e.g., a bony pressure point such as the greater trochanter or the sacrum). The term "partial thickness wound" refers to wounds that are limited to the epidermis and dermis; a wound of any etiology may be partial thickness. The term "full thickness wound" is meant to include wounds that extend through the dermis.

As used herein, "wound site" refers broadly to the anatomical location of a wound, without limitation.

As used herein, the term "dressing" refers broadly to any material applied to a wound for protection, absorbance, drainage, treatment, etc. Numerous types of dressings are commercially available, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), and cellophane (cellulose with a plasticizer) (Kannon and Garrett (1995) Dermatol. Surg. 21:583-590; Davies (1983) Burns 10:94; each herein incorporated by reference). The present disclosure also contemplates the use of dressings impregnated with pharmacological compounds (e.g., antibiotics, antiseptics, thrombin, analgesic compounds, etc). Cellular wound dressings include commercially available materials such as Apligraf®, Dermagraft®, Biobrane®, TransCyte®, Integra® Dermal Regeneration Template®, and OrCell®.

As used herein, the term "toxic" refers to any detrimental or harmful effects on a subject, a cell, or a tissue as compared to the same cell or tissue prior to the administration of the toxicant.

As used herein, the term "pharmaceutical composition" refers to the combination of an active agent (e.g., a ymgC polypeptide) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "topically" refers to application of the compositions of the present disclosure to the surface of the skin and mucosal cells and tissues (e.g., alveolar, buccal, lingual, masticatory, or nasal mucosa, and other tissues and cells which line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also can include stabilizers and preservatives. For examples of carriers, stabilizers, and adjuvants. (See e.g., Martin, Remington's Pharmaceutical Sciences, 15th Ed., Mack Publ. Co., Easton, Pa. (1975), incorporated herein by reference). In certain embodiments, the compositions of the present disclosure may be formulated for veterinary, horticultural or agricultural use. Such formulations include dips, sprays, seed dressings, stem injections, sprays, and mists. In certain embodiments, compositions of the present disclosure may be used in any application where it is desirable to alter (e.g., inhibit) the formation of biofilms, e.g., food industry applications; consumer goods (e.g., medical goods, goods intended for consumers with impaired or developing immune systems (e.g., infants, children, elderly, consumers suffering from disease or at risk from disease), and the like.

As used herein, the term "medical devices" includes any material or device that is used on, in, or through a subject's or patient's body, for example, in the course of medical treatment (e.g., for a disease or injury). Medical devices include, but are not limited to, such items as medical implants, wound care devices, drug delivery devices, and body cavity and personal protection devices. The medical implants include, but are not limited to, urinary catheters, intravascular catheters, dialysis shunts, wound drain tubes, skin sutures, vascular grafts, implantable meshes, intraocular devices, heart valves, and the like. Wound care devices include, but are not limited to, general wound dressings, biologic graft materials, tape closures and dressings, and surgical incise drapes. Drug delivery devices include, but are not limited to, needles, drug delivery skin patches, drug delivery mucosal patches and medical sponges. Body cavity and personal protection devices, include, but are not limited to, tampons, sponges, surgical and examination gloves, contact lenses, and toothbrushes. Birth control devices include, but are not limited to, intrauterine devices (IUDs), diaphragms, and condoms.

As used herein, the term "therapeutic agent," refers to compositions that decrease the infectivity, morbidity, or onset of mortality in a subject (e.g., a subject contacted by a biofilm-forming microorganism) or that prevent infectivity, morbidity, or onset of mortality in a host contacted by a biofilm-forming microorganism. As used herein, therapeutic agents encompass agents used prophylactically, e.g., in the absence of a biofilm-forming organism, in view of possible future exposure to a biofilm-forming organism. Such agents may additionally comprise pharmaceutically acceptable compounds (e.g., adjuvants, excipients, stabilizers, diluents, and the like). In some embodiments, the therapeutic agents of the present disclosure are administered in the form of topical compositions, injectable compositions, ingestible compositions, and the like. When the route is topical, the form may be, for example, a solution, cream, ointment, salve or spray.

The term "coating" as used herein refers to a layer of material covering, e.g., a medical device or a portion thereof. A coating can be applied to the surface or impregnated within the material of the implant.

As used herein, the term "antimicrobial agent" refers to composition that decreases, prevents or inhibits the growth of bacterial and/or fungal organisms. Examples of antimicrobial agents include, e.g., antibiotics and antiseptics and ymgC polypeptides.

The term "antiseptic" as used herein is defined as an antimicrobial substance that inhibits the action of microorganisms, including but not limited to α-terpineol, methylisothiazolone, cetylpyridinium chloride, chloroxyleneol, hexachlorophene, chlorhexidine and other cationic biguanides, methylene chloride, iodine and iodophores, triclosan, taurinamides, nitrofurantoin, methenamine, aldehydes, azylic acid, silver, benzyl peroxide, alcohols, and carboxylic acids and salts. One skilled in the art is cognizant that these antiseptics can be used in combinations of two or more to obtain a synergistic or additive effect. Some examples of combinations of antiseptics include a mixture of chlorhexidine, chlorhexidine and chloroxylenol, chlorhexidine and methylisothiazolone, chlorhexidine and (α-terpineol, methylisothiazolone and α-terpineol; thymol and chloroxylenol; chlorhexidine and cetylpyridinium chloride; or chlorhexidine, methylisothiazolone and thymol. These combinations provide a broad spectrum of activity against a wide variety of organisms.

The term "antibiotics" as used herein is defined as a substance that inhibits the growth of microorganisms, preferably without damage to the host. For example, the antibiotic may inhibit cell wall synthesis, protein synthesis, nucleic acid synthesis, or alter cell membrane function.

Classes of antibiotics include, but are not limited to, macrolides (e.g., erythromycin), penicillins (e.g., nafcillin), cephalosporins (e.g., cefazolin), carbepenems (e.g., imipenem), monobactam (e.g., aztreonam), other beta-lactam antibiotics, beta-lactam inhibitors (e.g., sulbactam), oxalines (e.g. linezolid), aminoglycosides (e.g., gentamicin), chloramphenicol, sufonamides (e.g., sulfamethoxazole), glycopeptides (e.g., vancomycin), quinolones (e.g., ciprofloxacin), tetracyclines (e.g., minocycline), fusidic acid, trimethoprim, metronidazole, clindamycin, mupirocin, rifamycins (e.g., rifampin), streptogramins (e.g., quinupristin and dalfopristin) lipoprotein (e.g., daptomycin), polyenes (e.g., amphotericin B), azoles (e.g., fluconazole), and echinocandins (e.g., caspofungin acetate).

Examples of specific antibiotics include, but are not limited to, erythromycin, nafcillin, cefazolin, imipenem, aztreonam, gentamicin, sulfamethoxazole, vancomycin, ciprofloxacin, trimethoprim, rifampin, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, linezolid, temafloxacin, tosufloxacin, clinafloxacin, sulbactam, clavulanic acid, amphotericin B, fluconazole, itraconazole, ketoconazole, and nystatin. Other examples of antibiotics, such as those listed in Sakamoto et al, U.S. Pat. No. 4,642,104 herein incorporated by reference will readily suggest themselves to those of ordinary skill in the art.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Such examples are not however to be construed as limiting the sample types applicable to the present disclosure.

DETAILED DESCRIPTION OF THE DISCLOSURE

Provided herein are compositions and methods for generation of cysteine in microbial systems. Further provided herein are compositions and methods for reducing and eliminating biofilms.

As described in Example 1 below, experiments conducted during the course of development of embodiments of the present disclosure determined that E. coli ymgC inhibits CysE, a component of the cysteine biosynthetic pathway. Accordingly, provided herein are host cells lacking functional ymgC genes for production of cysteine.

Further experiments determined that ymgC is an inhibitor of biofilm formation in E. coli. Accordingly, further provided herein are ymgC polypeptides for use as biofilm inhibitors in vitro and in vivo.

I. Production of Cysteine

In some embodiments, the present disclosure provides compositions and method for the production of cysteine in microbial (e.g., E. coli) expression systems.

In some embodiments, bacteria (e.g., E. coli) for production of cysteine are engineered to lack a functional ymgC gene. In some embodiments, the ymgC gene is mutated to result in a non-functional or non-expressed gene product. In some embodiments, the ymgC gene is deleted or knocked out.

In some embodiments, mutation or removal of the ymgC gene results in increased levels of cysteine relative to bacteria with a functional ymgC gene (e.g., the levels of cysteine are at least 1.5 times, 2 times, 5 times, 10 times or more the level in bacteria with a functional ymgC gene).

In some embodiments, strains are modified to lack a functional poxB, glgC, ymgC, tnaA, pgaC, yaiP, ugD, ptA, ldhA, ashe, and/or pflB gene. In some embodiments, strains are modified to overexpress metH and/or yjeH.

Any suitable method for mutating or removing the ymgC (or other genes described herein) gene is contemplated for use in the compositions and methods described herein. Gene knock out or mutation may be accomplished using any suitable method, including but not limited to, homologous recombination. Additional gene knock out techniques include, but are not limited to, the group II intron system referred to as ClosTron (Heap et al., Journal of Microbiological Methods, 2007. 70: p. 452-464; herein incorporated by reference in its entirety), multimeric, suicide plasmids (O'Brien and Melville, Infection and Immunity, 2004. 72 (9): p. 5204-5215; herein incorporated by reference in its entirety) and monomeric suicide plasmids (Green et al. Microbiology, 1996. 142 (pt. 8): p. 2079-2086; herein incorporated by reference in its entirety). RNA interference techniques include complementary RNA sequences (of variable length) that create double stranded RNA, which is either targeted for degradation or inhibits translation (Desai and Papoutsakis, Applied and Environmental Microbiology, 1999. 65 (3): p 936-945; herein incorporated by reference in its entirety), and longer interference RNA that take in consideration terminal unpaired nucleotides, components, and loop degree of the resulting interference RNA (Tummala, Welker and Papoutsakis, Journal of Bacteriology, 2003. 185 (6): p 1923-1934; herein incorporated by reference in its entirety).

In some embodiments, homologous recombination is used to disrupt the function of ymgC. Homologous recombination is routinely employed in molecular biology for a multitude of applications such as inserting recombinant genes into a host chromosome, targeting host genes for inactivation, and engineering host-reporter fusion proteins. More elegant genetic manipulation approaches employ homologous recombination to accelerate horizontal gene transfer (also known as lateral gene transfer) (Frost et al., Nat Rev Microbiol, 2005. 3 (9): p. 722-32; Gogarten and Townsend, Nat Rev Microbiol, 2005. 3 (9): p. 679-87; Smets and Barkay, Nat Rev Microbiol, 2005. 3 (9): p. 675-8; Sorensen et al., Nat Rev Microbiol, 2005. 3 (9): p. 700-10; Thomas and Nielsen, Nat Rev Microbiol, 2005. 3 (9): p. 711-21).

In some embodiments, CRISPR/Cas9 systems are used to delete or knock out genes. Clustered regularly interspaced short palindromic repeats (CRISPR) are segments of prokaryotic DNA containing short, repetitive base sequences. These play a key role in a bacterial defense system, and form the basis of a genome editing technology known as CRISPR/Cas9 that allows permanent modification of genes within organisms.

In some embodiments, function of a ymgC gene is disrupted using nucleic acid interference methods (e.g., antisense RNA, and related methods).

The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is decreasing the amount of ymgC expressed.

In some embodiments, nucleic acids are RNAi nucleic acids. "RNA interference (RNAi)" is the process of sequence-specific, post-transcriptional gene silencing initiated by a small interfering RNA (siRNA), shRNA, or microRNA (miRNA). During RNAi, the RNA induces degradation of target mRNA with consequent sequence-specific inhibition of gene expression.

In "RNA interference," or "RNAi," a "small interfering RNA" or "short interfering RNA" or "siRNA" or "short hairpin RNA" or "shRNA" molecule, or "miRNA" an RNAi (e.g., single strand, duplex, or hairpin) of nucleotides is targeted to a nucleic acid sequence of interest, for example, ymgC.

An "RNA duplex" refers to the structure formed by the complementary pairing between two regions of a RNA molecule. The RNA using in RNAi is "targeted" to a gene in that the nucleotide sequence of the duplex portion of the RNAi is complementary to a nucleotide sequence of the targeted gene. In certain embodiments, the RNAi is targeted to the sequence encoding ymgC. In some embodiments, the length of the RNAi is less than 30 base pairs. In some embodiments, the RNA can be 32, 31, 30, 29, 28, 27, 26, 25, 24, 23, 22, 21, 20, 19, 18, 17, 16, 15, 14, 13, 12, 11 or 10 base pairs in length. In some embodiments, the length of the RNAi is 19 to 32 base pairs in length. In certain embodiment, the length of the RNAi is 19 or 21 base pairs in length.

In some embodiments, RNAi comprises a hairpin structure (e.g., shRNA). In addition to the duplex portion, the hairpin structure may contain a loop portion positioned between the two sequences that form the duplex. The loop can vary in length. In some embodiments the loop is 5, 6, 7, 8, 9, 10, 11, 12, 13, 14, 15, 16, 17, 18, 19, 20, 21, 22, 23, 24, 25, 26 or 27 nucleotides in length. In certain embodiments, the loop is 18 nucleotides in length. The hairpin structure can also contain 3' and/or 5' overhang portions. In some embodiments, the overhang is a 3' and/or a 5' overhang 0, 1, 2, 3, 4 or 5 nucleotides in length.

"miRNA" or "miR" means a non-coding RNA between 18 and 25 nucleobases in length which hybridizes to and regulates the expression of a coding RNA. In certain embodiments, a miRNA is the product of cleavage of a pre-miRNA by the enzyme Dicer. Examples of miRNAs are found in the miRNA database known as miRBase.

As used herein, Dicer-substrate RNAs (DsiRNAs) are chemically synthesized asymmetric 25-mer/27-mer duplex RNAs that have increased potency in RNA interference compared to traditional RNAi. Traditional 21-mer RNAi molecules are designed to mimic Dicer products and therefore bypass interaction with the enzyme Dicer. Dicer has been recently shown to be a component of RISC and involved with entry of the RNAi into RISC. Dicer-substrate RNAi molecules are designed to be optimally processed by Dicer and show increased potency by engaging this natural processing pathway. Using this approach, sustained knockdown has been regularly achieved using sub-nanomolar concentrations. (U.S. Pat. No. 8,084,599; Kim et al., Nature Biotechnology 23:222 2005; Rose et al., Nucleic Acids Res., 33:4140 2005).

The transcriptional unit of a "shRNA" is comprised of sense and antisense sequences connected by a loop of unpaired nucleotides. shRNAs are exported from the nucleus by Exportin-5, and once in the cytoplasm, are processed by Dicer to generate functional RNAi molecules. "miRNAs" stem-loops are comprised of sense and antisense sequences connected by a loop of unpaired nucleotides typically expressed as part of larger primary transcripts (pri-miRNAs), which are excised by the Drosha-DGCR8 complex generating intermediates known as pre-miRNAs, which are subsequently exported from the nucleus by Exportin-5, and once in the cytoplasm, are processed by Dicer to generate functional miRNAs or siRNAs.

"Artificial miRNA" or an "artificial miRNA shuttle vector", as used herein interchangeably, refers to a primary miRNA transcript that has had a region of the duplex stem loop (at least about 9-20 nucleotides) which is excised via Drosha and Dicer processing replaced with the siRNA sequences for the target gene while retaining the structural elements within the stem loop necessary for effective Drosha processing. The term "artificial" arises from the fact the flanking sequences (e.g., about 35 nucleotides upstream and about 40 nucleotides downstream) arise from restriction enzyme sites within the multiple cloning site of the RNAi. As used herein the term "miRNA" encompasses both the naturally occurring miRNA sequences as well as artificially generated miRNA shuttle vectors.

The RNAi can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal or a sequence of six Ts.

In some embodiments, bacteria (e.g., *E. coli*) lacking functional ymgC genes are used to generate cysteine using fermentation methods. Exemplary methods of fermentative production of cysteine by microorganisms are described, e.g., in U.S. Pat. Nos. 6,218,168B1, 5,972,663A, US20040038352A1, CA2386539A1, US20090053778A1 and US20090226984A1; each of which is herein incorporated by reference in its entirety.

In some embodiments, the yield of cysteine yield in the fermentation is further increased by attenuating or destroying genes which encode cysteine-degrading enzymes, such as, e.g., the tryptophanase TnaA or the cystathionine β-lyases MalY or MetC (See e.g., EP1571223; herein incorporated by reference in its entirety).

In some embodiments, the transport of cysteine out of the cell is increased in order to increase the product yield in the medium. This can be achieved by overexpression of what are termed efflux genes. These genes encode membrane-bound proteins which mediate the export of cysteine out of the cell. Various efflux genes have been described for cysteine export (U.S. Pat. No. 5,972,663A, US20040038352A1; each of which is herein incorporated by reference in its entirety).

In some embodiments, cysteine is produced in a bioreactor, for example, a stirred-tank fermenter, having a volume of at least 5 m$^3$. Culturing the cysteine-producing cells is typically carried out in a plurality of stages. Proceeding from a stock culture, the cells are initially grown in at least one preculture before the main culture is inoculated with the last preculture. In this case, generally a successive scale-up proceeds from shake flask via fermenters on a laboratory scale up to the bioreactor on an industrial scale.

In some embodiments, cysteine producing cells are grown under aerobic growth conditions, wherein the oxygen content during the fermentation in the main culture is set at a maximum 50% saturation. The oxygen saturation in the culture is in this case regulated automatically via the gas feed and the stirring speed.

In some embodiments, culture media further comprises a carbon source. Examples include, but are not limited to, sugars, sugar alcohols, organic acids or sugar-containing plant hydrolysates. Specific examples include, but are not limited to glucose, fructose, lactose, glycerol or mixtures which comprise two or more of these compounds.

In some embodiments, the carbon source is added to the main culture in such a manner that the content of the carbon source in the fermenter does not exceed 10 g/l (e.g., less than 5 g/g or 0.1 g/1) during the production phase.

In some embodiments, a nitrogen source is added to the culture medium. Examples include, but are not limited to, ammonia, ammonium salts or protein hydrolysates.

As further media additives, salts of the elements phosphorus, chlorine, sodium, magnesium, nitrogen, potassium, calcium, iron, and, in traces salts of the elements molybdenum, boron, cobalt, manganese, zinc and nickel can be added.

In addition, organic acids (e.g. acetate, citrate) and vitamins (e.g. B1, B6) can be added to the medium.

As complex nutrient sources, e.g. yeast extract, corn steep liquor, soybean flour or malt extract can be used.

The incubation temperature for mesophilic microorganisms such as, e.g., *E. coli* is generally 15-45° C. (e.g., 30-37° C.).

The pH of the fermentation medium is typically in the pH range from 5.5 to 7.5 during the fermentation.

For the production of L-cysteine and L-cysteine derivatives, during the fermentation a sulfur source should be supplied (e.g., sulfates or thiosulfates).

In some embodiments, bacteria described herein are provided in a kit or system (e.g., in combination with culture medium, reaction vessels, carbon sources, temperature control systems, atmospheric control systems, etc.).

II. Anti-Biofilm Compositions

In some embodiments, the present disclosure provides compositions and methods comprising ymgC polypeptides (e.g., for use in killing or preventing the growth of biofilms).

A biofilm is an aggregate of microorganisms in which cells adhere to each other and/or to a surface. These adherent cells are frequently embedded within a self-produced matrix of extracellular polymeric substance (EPS). Biofilm EPS, also referred to as slime, is a polymeric conglomeration generally composed of extracellular DNA, proteins, and polysaccharides in various configurations and of various compositions. Biofilms may form on living or non-living surfaces, and represent a prevalent mode of microbial life in natural, industrial and clinical settings. The microbial cells growing in a biofilm are physiologically distinct from planktonic cells of the same organism, which, by contrast, are single cells that may float or swim in a liquid medium.

Microbial biofilms form in response to many factors including but not limited to cellular recognition of specific or non-specific attachment sites on a surface, nutritional cues, or in some cases, by exposure of planktonic cells to sub-inhibitory concentrations of antibiotics. When a cell switches to the biofilm mode of growth, it undergoes a phenotypic shift in behavior in which large suites of genes are differentially regulated (Petrova et al., J. Bacteriol. 2012 May; 194 (10): 2413-25; Stoodley et al., Annu Rev Microbiol. 2002; 56:187-209).

Although the present disclosure is not limited by any type of biofilm, biofilm formation typically begins with the attachment of free-floating microorganisms to a surface. These first colonists adhere to the surface initially through weak, reversible Van der Waals forces. If the colonists are not immediately separated from the surface, they can anchor themselves more permanently using cell adhesion structures such as pili.

Initial colonists commonly facilitate the arrival of other cells by providing more diverse adhesion sites and beginning to build the matrix that holds the biofilm together. Some species are not able to attach to a surface on their own but are often able to anchor themselves to the matrix or directly to earlier colonists. It is during this colonization that the cells are able to communicate via quorum sensing, for example, using such compounds as AHL. Once colonization initiates, the biofilm grows through a combination of cell division and recruitment. The final stage of biofilm formation is known as development although herein the terms "formation" and "development" are used interchangeably. In this final stage, the biofilm is established and may only change in shape and size. The development of a biofilm may allow for an aggregate cell colony (or colonies) to be increasingly antibiotic resistant.

Dispersal of cells from the biofilm colony is an essential stage of the biofilm lifecycle. Dispersal enables biofilms to spread and colonize new surfaces. Enzymes that degrade the biofilm extracellular matrix, such as dispersin B and deoxyribonuclease, may play a role in biofilm dispersal (Whitchurch et al. (2002) Science 295:1487; herein incorporated by reference in its entirety). Biofilm matrix degrading enzymes may be useful as anti-biofilm agents (Kaplan et al. (2004) Antimicrobial Agents and Chemotherapy 48 (7): 2633-6; Xavier et al. (2005) Microbiology 151 (Pt 12): 3817-32; each herein incorporated by reference in its entirety). A fatty acid messenger, cis-2-decenoic acid, can induce dispersion and inhibiting growth of biofilm colonies. Secreted by *Pseudomonas aeruginosa*, this compound induces dispersion in several species of bacteria and the yeast *Candida albicans* (Davies et al. (2009) Journal of Bacteriology 191 (5): 1393-403; herein incorporated by reference in its entirety).

Biofilms are ubiquitous and are usually found on solid substrates submerged in or exposed to some aqueous solution, although they can form as floating mats on liquid surfaces and also on the surface of leaves, particularly in high humidity climates. Given sufficient resources for growth, a biofilm will quickly grow to be macroscopic. Many types of microbes can form biofilms, e.g., bacteria, archaea, protozoa, fungi and algae. Biofilms may comprise a single type of microbe (monospecies biofilms), or, commonly, multiple types. In some mixed species biofilms, each group performs specialized metabolic functions.

Biofilms form in environments including but not limited to: substrates (e.g., rocks, pebbles) in natural bodies of water (e.g., rivers, pools, streams, oceans, springs); extreme environments (e.g., hot springs including waters with extremely acidic or extremely alkaline pH; frozen glaciers); residential and industrial settings in which solid surfaces are exposed to liquid (e.g., showers, water and sewage pipes, floors and counters in food preparation or processing areas, water-cooling systems, marine engineering systems); hulls and interiors of marine vessels; sewage and water treatment facilities (e.g., water filters, pipes, holding tanks); contaminated waters; within or upon living organisms (e.g., dental plaque, surface colonization or infection of e.g., skin, surfaces of tissues or organs or body cavities or at wound sites; plant epidermis, interior of plants); on the inert surfaces of implanted devices such as catheters, prosthetic cardiac valves, artificial joints, and intrauterine devices; and the like.

Biofilms are involved in a wide variety of microbial infections in the body. Infectious processes in which biofilms have been implicated include but are not limited to urinary tract infections, catheter infections, middle-ear infections, formation of dental plaque and gingivitis, contact lens contamination (Imamura et al. (2008) Antimicrobial Agents and Chemotherapy 52 (1): 171-82; herein incorporated by reference in its entirety), and less common but more lethal processes such as endocarditis, infections in cystic fibrosis, and infections of permanent indwelling devices such as joint prostheses and heart valves (Lewis et al. (2001) Antimicrobial Agents and Chemotherapy 45 (4): 999-1007; Parsek et al. (2003) Annual Review of Microbiology 57:677-701; each herein incorporated by reference in its entirety). Bacterial biofilms may impair cutaneous wound healing and reduce topical antibacterial efficiency in healing or treating infected skin wounds (Davis et al. (2008) Wound Repair and Regeneration 16 (1): 23-9; herein incorporated by reference in its entirety).

In some embodiments, the present disclosure provides compositions comprising a ymgC polypeptide, alone or in combination with a pharmaceutically acceptable carrier or other desired delivery material (e.g., cleaner or disinfectant, etc.).

In some embodiments, the ymgC polypeptide is a variant, mimetic, fragment, or other modified form of ymgC (e.g., ymgC described by Uniprot P75994; MNNSIPERFIFOCALFKNLEREVFMTHGYVDSHIIDOALRLRLK-DETSVILSDLYLQIL QYIEMHKTTLTDIIINDRESVLS; SEQ ID NO: 1). In some embodiments, the variant or fragment of ymgC maintains anti-biofilm activity. In some embodiments, variants comprise one or more amino acid changes (e.g., conservative or non-conservative changes). In some embodiments, variants are at least 80% (e.g., at least 80, 85, 90, 95, 96, 97, 98, or 99%) identical to wild type ymgC. In some embodiments, fragments comprise at least 5 amino acids (e.g., at least 5, 10, 50, 100 or up to the full length ymgC polypeptides minus 1 amino acid) of ymgC. In some embodiments, candidate ymgC polypeptides are assayed for activity using the methods described in Example 1 or using another suitable method.

Pharmaceutical compositions and formulations for topical administration may include transdermal patches, ointments, lotions, creams, gels, drops, suppositories, sprays, liquids, mouthwash, and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present disclosure include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations, which may conveniently be presented in unit dosage form, may be prepared according to conventional techniques well known in the pharmaceutical industry.

The compositions may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions, such as dyes, flavoring agents, preservatives, antioxidants, opacifiers, thickening agents and stabilizers. However, such materials, when added, should not unduly interfere with the biological activities of the components of the compositions. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the active agents of the formulation.

In some embodiments, the pharmaceutical composition contains a) ymgC polypeptides, and b) one or more other agents useful in killing or preventing the growth of microorganisms (e.g., antibiotics) or impacting the growth, formation or health impact or microorganisms in biofilms.

In some embodiments, the present disclosure provides kits, pharmaceutical compositions, or other delivery systems for use of ymgC polypeptides in treating or preventing bacterial infections or biofilms present on surfaces. The kit may include any and all components necessary, useful or sufficient for research or therapeutic uses including, but not limited to, ymgC polypeptides, pharmaceutical carriers, and additional components useful, necessary or sufficient for treating or preventing bacterial infections. In some embodiments, the kits provide a sub-set of the required components, wherein it is expected that the user will supply the remaining components. In some embodiments, the kits comprise two or more separate containers wherein each container houses a subset of the components to be delivered. Optionally, compositions and kits comprise other active components in order to achieve desired therapeutic effects.

In some embodiments, pharmaceutical compositions are administering in a maintenance or ongoing manner (e.g., one or more times a day, two or more times a day, one or more times a week, etc.). In some embodiments, compositions are administered continuously (e.g., via a skin patch, bandage, or time release formulation). In some embodiments, compositions are administered once, twice, 5 times, 10 times or more. In some embodiments, compositions are administered over a period of weeks, months, years or indefinitely In some embodiments, ymgC polypeptides or compositions comprising ymgC polypeptides find use in the decontamination of medical devices (e.g., catheters, speculums, and the like) or implantable medical devices (e.g., pacemakers, internal defibrillators, artificial joints or bones and the like).

In some embodiments, ymgC polypeptides or compositions comprising ymgC polypeptides find use in the decontamination of surfaces (e.g., surfaces comprising biofilms). Examples include but are not limited to, household surfaces, hospital or clinical surfaces (e.g., exam tables, operating rooms, etc.), and the like.

In some embodiments, ymgC polypeptides or compositions comprising ymgC polypeptides find use in the decontamination or protection of food or food preparation areas. For example, in some embodiments, ymgC polypeptides are applied to a food after harvest to protect against future contamination or treat existing contamination.

EXPERIMENTAL

The following example is provided in order to demonstrate and further illustrate certain preferred embodiments and aspects of the present disclosure and are not to be construed as limiting the scope thereof.

Example 1

Materials and Methods
Ab Initio Structural Modeling and Predicted Functional Annotation As YmgC lacks any structurally characterized homologs sufficiently similar to it to serve as useful templates for structural modeling, five ab initio models of YmgC were generated using the QUARK webserver (Xu and Zhang, 2012). Each structure was subsequently utilized as input to the COFACTOR webserver (Roy et al., 2012), which provides predicted functional annotations on the basis of structural similarity. Both servers were run using default parameters.

Cell Strains and Growth Conditions:

For this study, the *E. coli* K-12 derivative W3110 was used as the genetic background unless otherwise noted. Single gene knockout mutants of ymgC::kan, cysE::kan and tnaA::kan were P1vir transduced (Garges, 1993) from the Keio collection (Baba et al., 2006) into *E. coli* W3110. In most cases the kanamycin resistance cassette was subsequently excised by transforming the cells with pCP20, inducing Flp recombinase expression, and subsequently growing the cells at 42° C. to remove the helper plasmid (Datsenko and Wanner, 2000) to yield the deletion mutants used in the study (and to allow marker recycling for construction of double mutants); see Table 1 for details. Proper antibiotics-containing LB plates were used to select the mutant, whose deletions were verified by PCR sizing. Cells expressing YmgC in trans were obtained by transformation with the ymgC-expression vector from the ASKA library (Kitagawa et al., 2005).

Both for standard cloning and the physiological experiments described here, Lennox-variant LB (10 g/L tryptone, 5 g/L peptone, 5 g/L NaCl) was used unless otherwise noted.
Purification of YmgC and CysE for CysE Activity Measurement:

The IMPACT™ kit (E6901S, New England BioLabs) was used to purify YmgC and CysE for use in enzymatic activity assays, allowing isolation of the protein of interest with minimal perturbation to the protein sequence due to the presence of a self-cleaving intein-chitin binding domain tag. Briefly, ymgC and cysE were cloned into the pTXB1 plasmid (the last amino acid of ymgC before stop codon was changed from Serine, TCT, to Threonine, ACG, for improved tag cleavage), confirmed by sequencing, and transferred into ER2566 cells (NEB). For production, one liter culture was grown in 37° C. to OD 600 nm 0.4, then cooled on ice for 30 min. IPTG was added to 500 µM, and growth continued for 5 hours more in 25° C. prior to harvesting the cells. The cells were lysed by sonication in HEGX buffer (20 mM HEPES-KOH PH 7.2, 0.8 M NaCl, 1 mM EDTA, 10% glycerol, 0.2% Triton X-100) plus protease inhibitors (Roche catalog #11697498001), centrifuged for 30 min 15000×g and the supernatant was collected. Then the supernatants were loaded on a 10-ml chitin column (NEB), washed with 150 ml HEGX buffer, then HEGX plus DTT to 100 mM was added and column left for 48 hours at 4° C. to cleave the intein-chitin tag. Then, the elution buffer was collected, dialyzed against HEPES-KOH PH 7.2, and concentrated (Amicon®Ultra-4 centrifugal filter, Millipore). The Bradford assay and SDS-PAGE silver staining were performed for the protein quantification and purity assessment.
CysE-His Tag Purification:

In some assays shown below, His-tagged CysE was use to enable the use of separate tags on CysE and YmgC. In this case, *E. coli* BL21 cells expressing cysE in trans by incorporation of cysE-expression vector from the ASKA library were cultured in one liter of LB in 37° C. When the OD 600 nm of cultures were 0.4, IPTG to 500 µM was added to the cultures. After 4 hours of additional growth (leaving the cultures in stationary phase), the cells were harvested, and lysed by sonication in HEGX buffer (see above). The lysates were pelleted by centrifugation for 30 min at 15000×g and their supernatants were collected. HisPur™ cobalt spin columns (Thermo Fisher Scientific) were used according to the manufacturer's instructions to purify CysE-Histag and the obtained CysE-Histag was concentrated (Amicon®Ultra-4 centrifugal filter, Millipore). Protein quantitation was performed using the Bradford method, and SDS-PAGE with silver staining performed for purity assessment.
Swarming Motility:

Swarm motility plate assays were performed as reported by Niu et al. (Niu et al., 2005) on LB plates supplemented with 0.65% Bacto agar and 0.03% Tween 20. The plates were inspected for bacterial growth and motility after an overnight incubation at room temperature.
Biofilm Formation Assay:

This assay was an adaptation of Pratt and Kolter assay (Pratt and Kolter, 1998). Briefly, cells were grown in polystyrene 96-well microtiter plates (catalog number 82.1581.001, Sarstedt) at 28° C. for 48 hours without shaking in 150 µl LB liquid medium, and their optical density at 600 nm measured to provide a proxy for cell growth. Then, microtiter plates were rinsed thoroughly with water twice, and the cells were stained with 0.1% crystal violet for 15 min, rinsed again with water and dried. The retained Crystal Violet was then solubilized by the addition of 100 µl of 70:30 ethanol/acetone (Lehnen et al., 2002) and quantified by spectrometry at 570 nm (O'Toole and Kolter, 1998). The biofilm content was normalized by cell growth (turbidity at 600 nm at the end of the 48) as described by Zhang et al. (Zhang et al., 2008). The (log-scaled) biofilm data were analyzed using a hierarchical Bayesian model in which the biological replicates for a given genotype were assumed to arise from a t-distribution with four degrees of freedom and a genotype-specific mean and variance; the observed technical replicate data points on each day were then drawn from a second t-distribution centered on the biological replicate mean, with 4 degrees of freedom and a technical replicate variance parameter jointly inferred across all genotypes. All parameters received uninformative priors, with posterior distributions fitted using JAGS (Plummer-Proceedings of the 3rd international workshop on and 2003, 2003).

CysE Activity Measurement and Analysis:

The serine acetyltransferase activity of purified CysE was determined by monitoring the absorbance increase of Ellman's reagent (DTNB) due to its reaction with CoA, as described in (Riddles et al., 1983). A 95 µl reaction mixture (50 mM Tris-HCl pH 7.4, 5 mM $MgCl_2$, 0.01 mM Acetyl-CoA, 10 mM L-Serine and 0.04 UM purified CysE protein) in a 96-well microtiter plate was incubated in a microplate reader (Epoch 2, Biotek) at 30° C. for 30 minutes. The absorbance values at a wavelength of 410 nm (Kumar et al., 2011) were obtained every 5 minutes. A blank control without L-Serine and Acetyl-CoA, and a positive control containing an excess of CoA (0.2 mM) only were included.

To obtain an effective inhibitory constant Ki for the effect of YmgC on CysE activity, a nonlinear mixed effects model was applied via the R lme4 package (Bates et al., 2015). At each of two fixed substrate concentrations (100 mM and 200 mM serine), the equation V=V max, eff/(1+ [Y mgC]/Ki)) (1) was fit with random effect terms added for the observed V max,eff at each biological replicate. Note that the V max, eff parameter does not reflect the true V max of the enzyme (e.g., in the context of the Michaelis-Menten equation), but rather the effective V that would be observed at a given substrate concentration in the absence of inhibitor. Confidence intervals in FIG. 2c were constructed via jackknife estimates of the experimental data points, treating each biological replicate as a single block and performing interval estimation on log-scaled data due to the non-negative nature of both parameters.

Growth Curve Measurements:

For growth curve, cells were pre-cultured overnight in 3 mL of LB with proper antibiotics, then diluted into LB media supplemented by IPTG (500 µM) such that their starting OD600 was ~0.01 and then the OD600 over time monitored and recorded, using standard spectrophotometry.

Glycogen Measurements:

For glycogen measurement, cells were pre-cultured overnight in 3 mL of LB with proper antibiotics, then diluted into LB media supplemented by IPTG (500 µM) such that their starting OD600 was ~0.01 and then the OD600 over time monitored and recorded during growth in a shaking incubator at 200 rpm and 37° C. When the cells reached an OD of 0.3, the cells were cultured for four hours to allow them to reach early stationary phase and then harvested. The harvested cells were centrifuged at 3500 rpm for 15 min at 4° C. and washed with 1× phosphate buffered saline (137 mM NaCl, 2.7 mM KCl, 10 mM $Na_2$ $HPO_4$, 1.8 mM $KH_2PO_4$, pH 7.4). Then, the cells were suspended in 50 mM Tris-HCl pH 7.4, sonicated, centrifuged for 15000×g 30 min at 4° C., and the supernatants were collected and glycogen content was quantified using an EnzyChrom™ Glycogen Assay Kit (BioAssay Systems) according to the manufacturer's instructions. Data were analyzed using a Bayesian multilevel model via the brms package (Bürkner, 2017); the log-scaled glycogen content was modeled as arising from linear terms due to the genotype and the day of the assay (as there was substantial covariance between all replicates performed on the same day), and a random effect-like term different for each biological replicate (drawn from a common distribution). The genotype and day parameters were assigned Normal (0,3) priors; default priors were used for all other parameters.

Figure 8B:
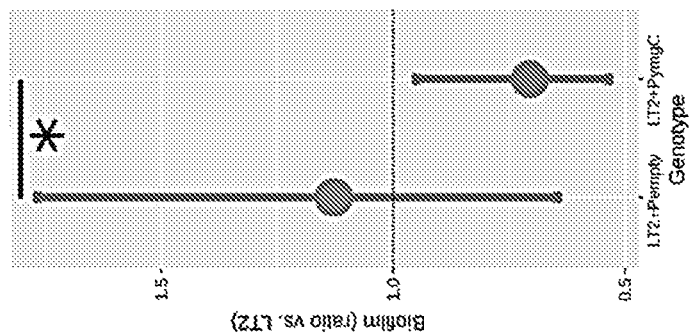
FIG. 8A through FIG. 8B shows effects of YmgC overexpression on biofilm formation in *S. typhymurium* LT2.

Biofilm Measurement in *S. typhimurium*:

Biofilm measurements on *S. typhimurium* LT2 cells were conducted using the same experimental procedure as described for *E. coli* above. The data were analyzed using a Bayesian multilevel model and the brms R package (Bürkner, 2017), fitting the log (biofilm normalized OD) values with a linear model on genotype, with random effects for both the biological replicate and the replicate: genotype interaction. FIG. 8b shows the posterior fitted value and 95% credible interval from the model.

Results

Aligning the predicted structure of YmgC to PDB data base shows a high similarity between serine acetyltransferase N-terminal domain and YmgC. To provide a starting point for determining the biological function of YmgC, a series of five ab initio structural models were generated for the protein, and subsequently used the COFACTOR webserver to predict their functions on the basis of structural homologs (Roy et al., 2012), as structural homology has proven to be a particularly useful ingredient in protein function prediction for cases with low sequence homologies to annotated targets (Zhang et al., 2017). The ab initio models of YmgC showed similar secondary structures with variations in the exact arrangement of the helical bundle formed (see FIG. 1a). While submitting the five models to COFACTOR did not yield a single consensus annotation, one striking repetition of a structural homolog was observed: for three out of the five QUARK models, the lists of structural homologs identified by COFACTOR included the serine acetyltransferase (SAT) enzyme of *Yersinia pestis* (PDB code 3GVD). Furthermore, for the highest-confidence QUARK model, 3GVD was the best structural analog identified. Upon further inspection, it was found that the YmgC models showed excellent structural alignments with the N-terminal domain of the *Y. pestis* SAT, with a 2.9 Å C∝RMSD despite having less than 7% sequence identity in the aligned region (see FIG. 1b). As the *Y. pestis* SATase shows >86% sequence identity to the *Escherichia coli* SAT CysE (based on alignment with Clustal Omega (Sievers et al., 2011)), a similar level of structural homology between *E. coli* YmgC and CysE is highly likely.

YmgC Acts as a Noncompetitive Inhibitor of CysE In Vitro

Figure 7:
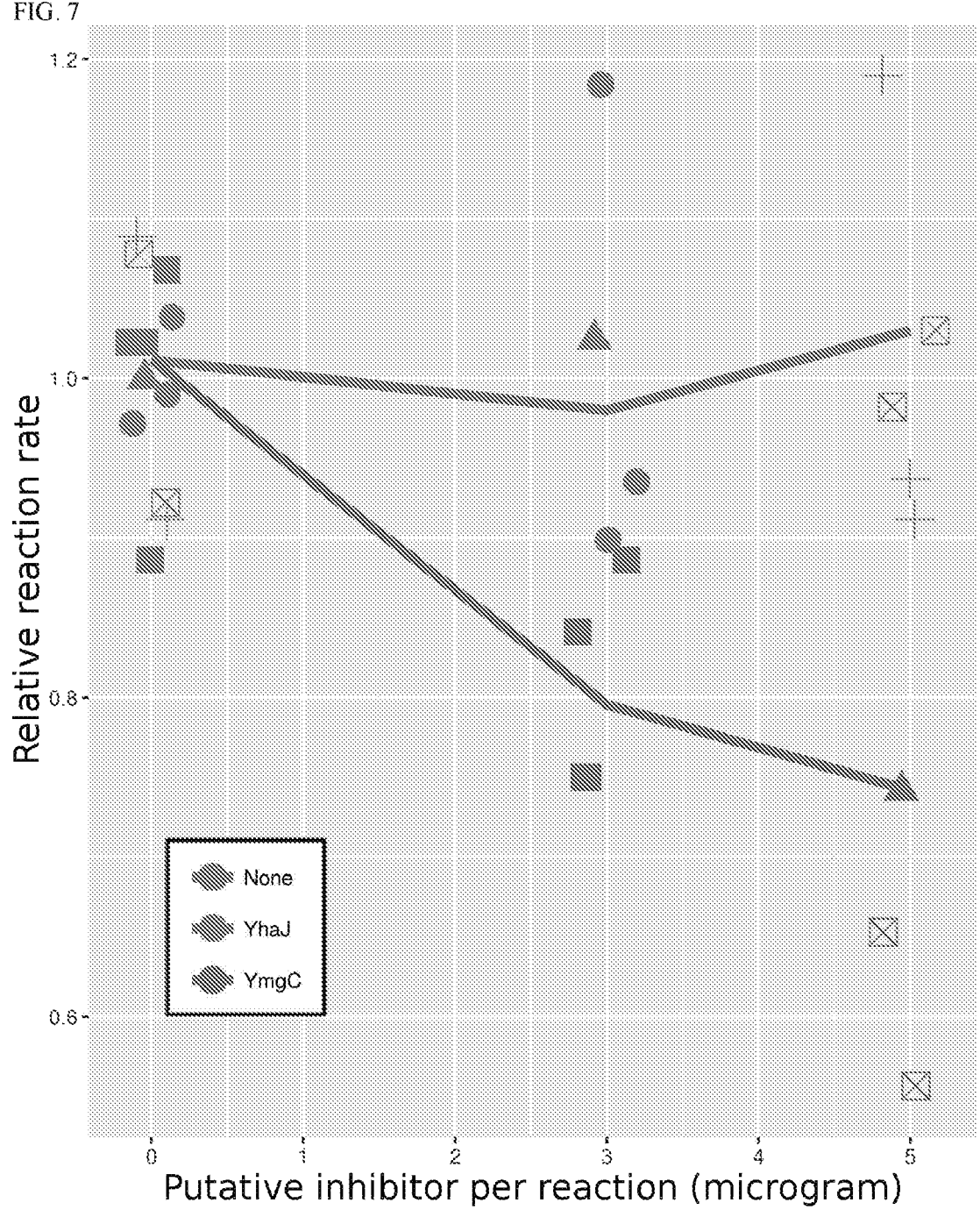
FIG. 7 shows a comparison of the effects of YmgC and YhaJ (a transcription factor that is not expected to interact with CysE) on CysE activity.

The N-terminal domain of serine acetyltransferase is a conserved sequence across the bacteria and plants (Saito et al., 1995). This domain plays a crucial role in the interaction of CysE monomers to form the hexamer structure of SAT and also assists the acetyl group transfer from acetyl-coA to serine (Pye et al., 2004), as shown in FIG. 1c. Given that YmgC shows a high structural similarity to N-domain of CysE, it was hypothesized that YmgC could function as an inhibitor of CysE, by disrupting oligomerization and/or through allosteric inhibition. To test this, the SAT enzyme activity of CysE was measured in the absence and presence of YmgC. As shown in FIG. 2a, the SAT enzyme activity is inhibited by adding YmgC to the enzymatic reaction, showing that YmgC inhibits CysE enzyme activity. Based on the different concentration of serine as a substrate of SAT enzyme and also different concentrations of YmgC in the reaction (FIG. 2b), a Ki of ~25 µM was calculated for inhibition of CysE by YmgC (FIG. 2c). It was also found that the inhibition by YmgC was non-competitive with respect to serine concentrations (FIG. 2b). In contrast, an E. coli transcription factor not expected to inhibit CysE (namely YhaJ), but purified identically to YmgC, showed no detectable inhibition of CysE (FIG. 7).

Co-Purification of YmgC with SAT Shows a Physical Interaction Between YmgC and SAT.

If YmgC inhibits CysE enzyme activity through the mechanisms hypothesized above, they should physically interact with each other. To test for a direct interaction between YmgC and CysE, a co-purification technique was used: as schematized in FIG. 3, either a YmgC-CBD (chitin binding domain) fusion or a YhaJ-CBD fusion was immobilized on a chitin column; YhaJ is an E. coli transcription factor (Palevsky et al., 2016) not expected to interact with CysE. The lysate of cells expressing His-tagged CysE was passed over the columns, the columns were washed thoroughly (see Methods), eluted by intein cleavage, and the resulting eluates were tested for SAT enzymatic activity. The hypothesis behind this experiment was if CysE monomer interacts with YmgC, some SAT activity enzyme should be observed after collecting YmgC but not with other proteins, and not with YmgC alone. It was observed that the lysate arising from attempted co-purification of CysE-His by YmgC-CBD showed SAT enzyme activity, whereas activity was dramatically lower for co-purification with the negative control YhaJ-CBD, and non-existent when YmgC-CBD was purified without the addition of CysE (FIG. 3); note that the moderate Ki of YmgC for CysE permits measurable activity even with copurified YmgC present. The results are consistent with the hypothesized physical interaction of YmgC with CysE.

The Absence of cysE Epistatically Masks the Effects of ymgC on Biofilm Formation It has been shown that the absence of ymgC causes a huge increase in biofilm formation (Lee et al., 2007a). It was also shown above that YmgC binds to CysE and inhibits its SAT enzyme activity. If this interaction is the primary path through which YmgC exerts its effects in vivo, one would expect that deletion of cysE should epistatically mask the phenotypes caused by changing ymgC expression status. To test this, the biofilm formation of ΔcysE, ΔcysE ymgC::Kan and ΔcysE ymgC O.E. mutants (the latter indicating overexpression of YmgC from an ASKA collection plasmid, as described in Methods) was tested. Consistent with our hypothesis, while the ymgC::Kan single mutant shows a higher biofilm content compared to WT (posterior probability >95%) and the ectopic expression of ymgC reverts the high biofilm formation phenotype of ymgC::Kan single mutant and WT (FIG. 4a), the ΔcysE, ΔcysEymgC::Kan and ΔcysE, ymgC O.E mutants showed similar biofilm content, showing that the effect of absence or over-expression of YmgC on biofilm is masked by the absence of CysE (FIG. 4a). In the other words, loss of CysE function epistatically masks the effects of YmgC.

It is also noteworthy that all ΔcysE mutants showed somewhat lower biofilm content than the WT cell, although the effects were not highly robust (posterior probabilities of reduced biofilm formation are 81% for ΔcysE, 76% for ΔcysE ymgC::Kan, and 69% for ΔcysE ymgC O.E), demonstrating that cysteine is a critical amino acid for biofilm formation in E. coli. Similar results have been observed in Vibrio fischeri in which the absence of cysteine cause negative effects on biofilm formation (Singh et al., 2015).

The Absence of CysE Epistatically Masks the Effect of Over-Expression of YmgC on Glycogen Biosynthesis and Growth.

Figure 5A:
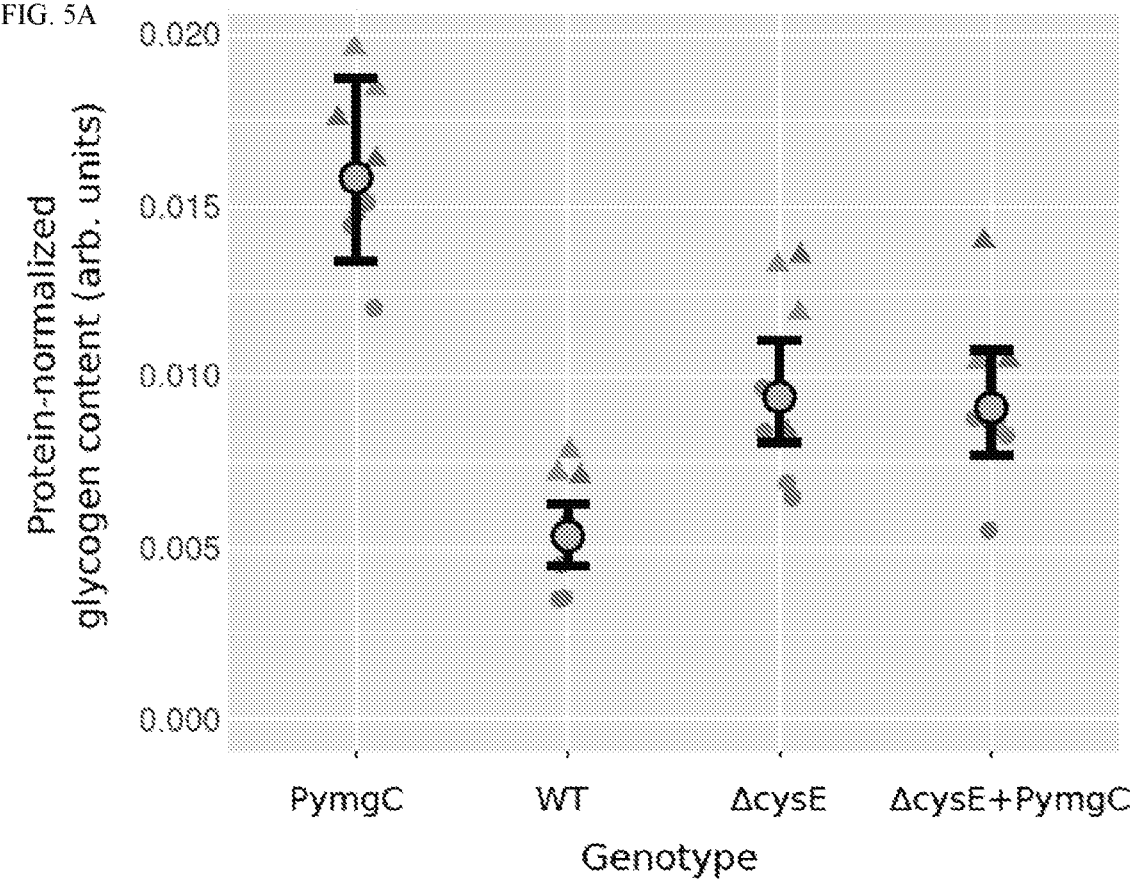
FIG. 5A through FIG. 5B shows interaction of YmgC overexpression and cysE deletion on glycogen production and cell growth.
Figure 5B:
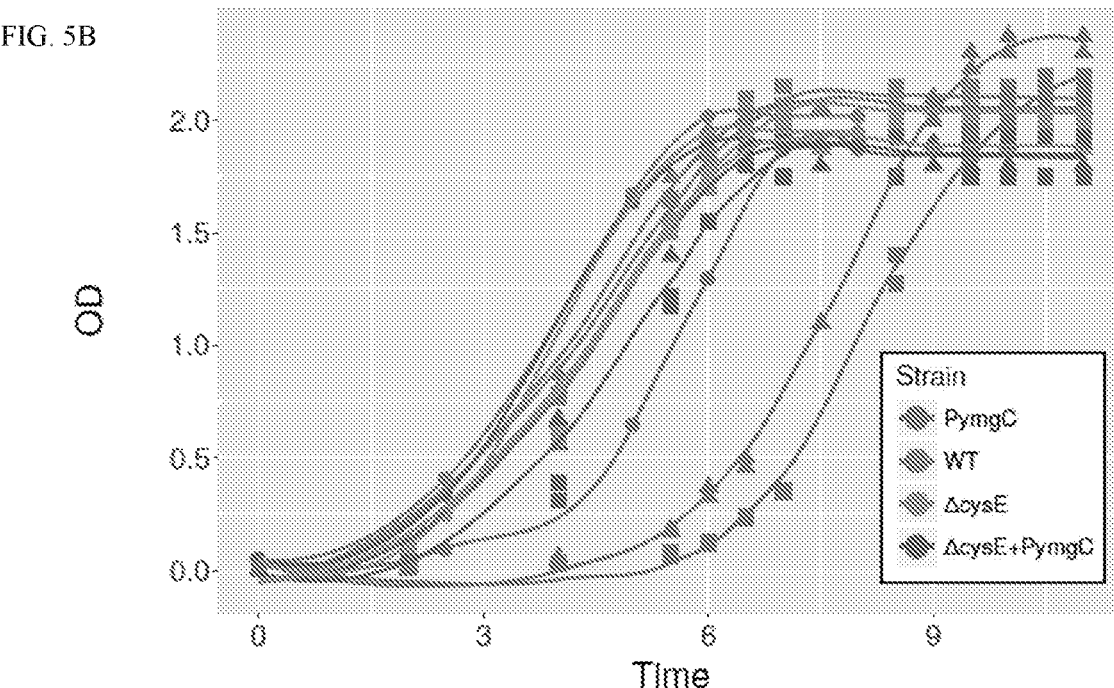
Figure 6A:
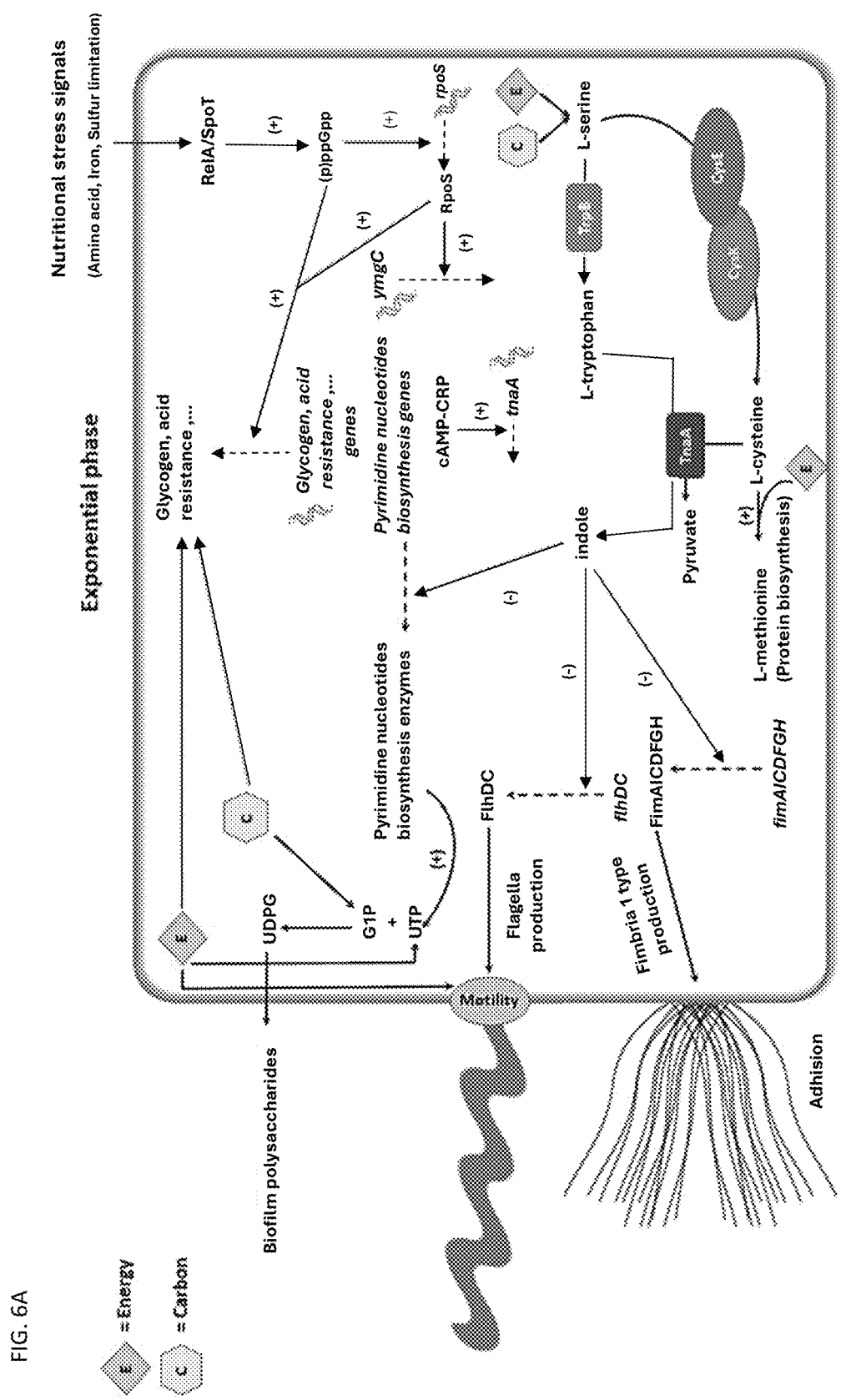
FIG. 6A through FIG. 6B shows a summary of proposed mechanisms through which YmgC regulates physiological state.
Figure 6B:
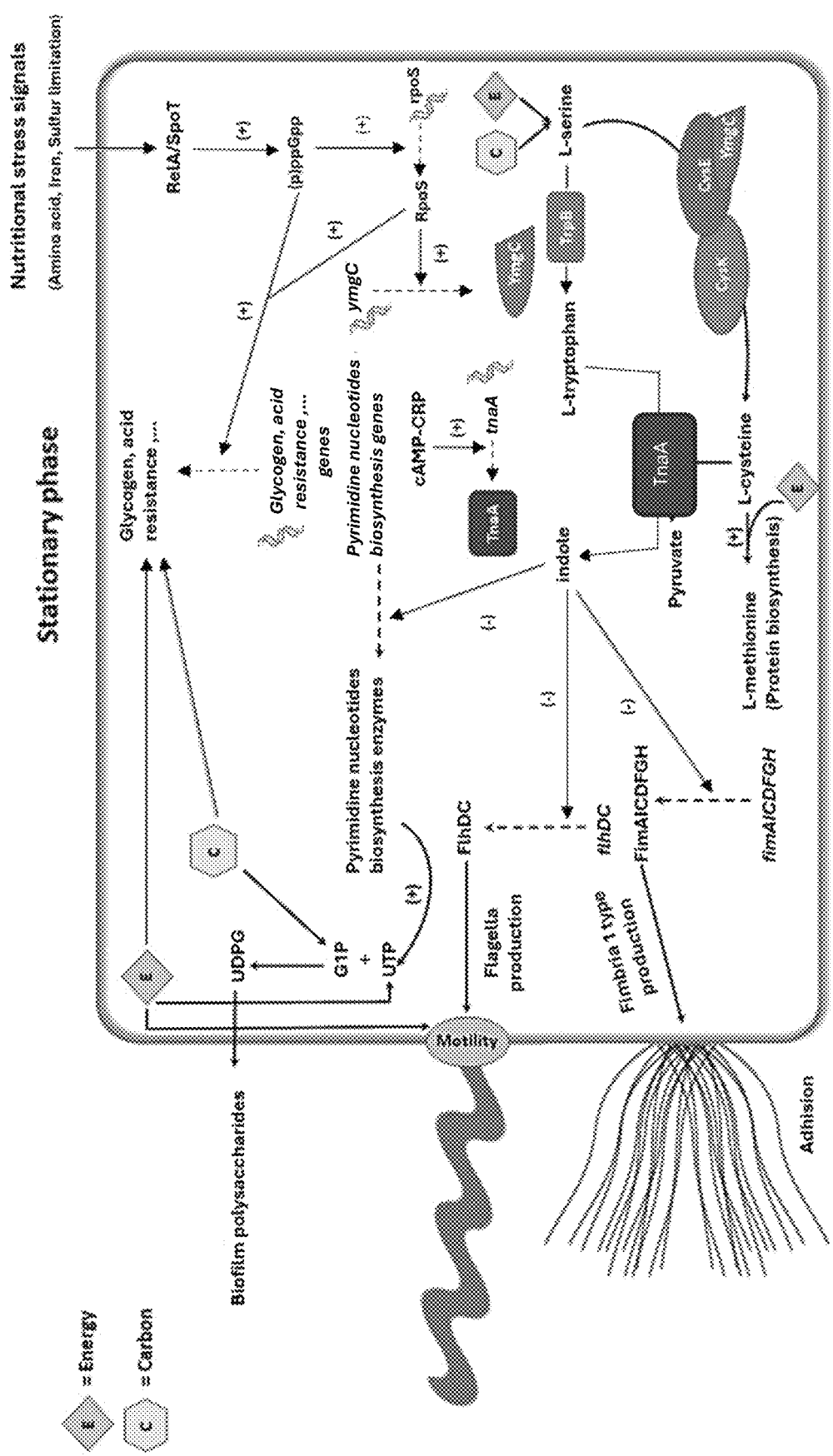

E. coli is able to synthesize glycogen, a branched intracellular homopolysaccharide α-1,4-linked glucose subunits with α-1,6-linkages at the branching points, which serves as an energy reserve and carbon source during stationary and lag phases (Yamamotoya et al., 2012). Several studies have shown that glycogen metabolism is linked to environmental survival, intestine colonization and virulence (Chang et al., 2004) (Jones et al., 2008) (Sambou et al., 2008) (Bourassa and Camilli, 2009) (Wang and Wise, 2011) and glycogen as an energy and carbon reserve is recognized an advantage of E. coli and Salmonella enteritidis (McMeechan et al., 2005). Like biofilm formation and swarming motility, which are highly energy and carbon consuming processes, glycogen biosynthesis requires carbon and energy. It has also been shown that the GlgC-controlled glycogen biosynthesis enzyme competes with swarming motility and biofilm exopolysaccharide biosynthesis for the same pools of ATP and glucose-1-phosphate during stationary phase (Rahimpour et al., 2013). The over-expression of YmgC in E. coli leads to a high glycogen content phenotype, indicating that YmgC must also somehow regulate glycogen biosynthesis (Eydallin et al., 2010). Significantly, several studies have shown that the absence of CysE and other genes involving in cysteine biosynthesis and transport cause a glycogen accumulation in E. coli (Eydallin et al., 2007; Montero et al., 2009). The computational and experimental studies described above demonstrate that YmgC interacts with CysE and inhibits its SAT activity, therefore it was determined that the reason why over-expression of YmgC in E. coli shows a high glycogen content is the inhibition of CysE and cysteine biosynthesis. Cysteine is also the only source of methionine biosynthesis (Ferla and Patrick, 2014), which is the most highly energy and carbon consuming amino acid biosynthesis process in E. coli (Stouthamer, 1973). Consistent with the hypothesis, the overexpression of YmgC in a ΔcysE mutant did not affect on the glycogen content of ΔcysE mutant (FIG. 5a), showing CysE function masks the high glycogen phenotype of the ymgC over-expression. It was also observed that the over-expression of YmgC in E. coli causes a long lag phase of the growth, but this effect is masked in a ΔcysE/ymgC overexpression strain (FIG. 5b). These results indicate that: (1) ectopic expression of YmgC has a negative impact on E. coli growth, and (2) the toxic effect of YmgC on the growth is through the inhibition of CysE function.

YmgC Shows a Reciprocal Sign Epistasis with the Dual-Function Tryptophanase Enzyme TnaA.

Serine, the substrate of CysE, is also is the substrate of TrpB enzyme, an enzyme involving in tryptophan biosynthesis of E. coli (Raboni et al., 2009). Tryptophan is then converted to indole through a multistage pathway including the TnaA enzyme (Li and Young, 2013; Newton et al., 1965).

Figure 4B:
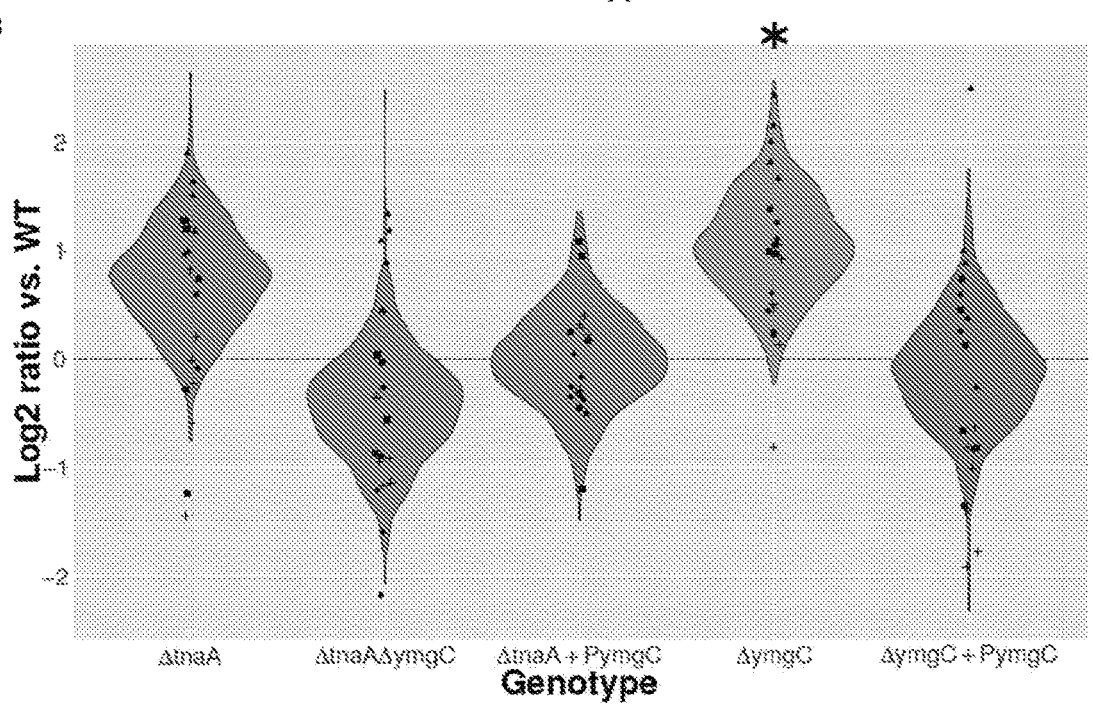

Indole is an intracellular and intercellular signal molecule synthesized at the onset of and during stationary phase, has a considerable effect on the global gene expression during stationary phase (Lee et al., 2007b). As reported, indole negatively regulates the expression of operons involved in pyrimidine nucleotide biosynthesis, flagellar biosynthesis, fimbriae biosynthesis (Bansal et al., 2007; Lee et al., 2008), but positively regulates the genes and operons involved in resistance to envelope stress, acid, and a variety of antibiotics (Hirakawa et al., 2005; Lee et al., 2010). TnaA is a dual function enzyme which also shows cysteine desulfhydrase activity (Awano et al., 2003, 2005), and thus TnaA can act along two pathways bringing it into potential biochemical interaction with YmgC: either directly through competition for serine with CysE, or indirectly by acting downstream of CysE in cysteine production. It was thus tested whether YmgC showed any genetic interaction with TnaA. As shown in FIG. 4b, while the ΔtnaA and ymgC::Kan single mutants each show higher biofilm content than WT (posterior probability 92% for ΔtnaA and 95% for ymgC::Kan), the ΔtnaA ymgC::Kan double mutant shows a biofilm formation phenotype less than or equal to that of WT (posterior probability of being less than WT is 60%; of being less than ymgC::Kan is 95%). This result shows a reciprocal sign epistasis between YmgC and TnaA, arising due to the complex interplay of these proteins in cysteine and serine metabolism, with the latter serving as the dominant cysteine desulfhydrase in *E. coli* (Snell, 1975).

Phenotypic effects of A ymgC mutants arise at least partly due to low indole levels.

In *E. coli*, 3-phosphoglycerate (3PG), which is an intermediate of carbon metabolism (glycolytic or gluconeogenic pathways) can be converted to serine (Mundhada et al., 2016; Pizer, 1963). It has been shown that during the transition from late exponential growth to onset of stationary phase, in *E. coli*, the expression of genes involving in cysteine metabolism suffers a huge repression (Bergholz et al., 2007). Also during growth in LB medium in aerobic conditions, at the onset of stationary phase, the expression of genes sufS and ycaC which encode cysteine desulfurase and cysteine hydrolase respectively, increases via RpoS (Patten et al., 2004) (the master regulator of general stress response and responsible for the transition of cells from exponential to stationary phases (Peano et al., 2015)), while the absence of rpoS enhances the cysteine production via an increase in the expression of cysE, cysK and cysD (Rahman et al., 2006). On the other hand, it has been shown that the existence of glucose post-transcriptionally inhibits the activity of pre-formed TnaA (Li and Young, 2014). With attention to these studies, it was observed that the serine conversion to cysteine pathway is more active during exponential phase, and less so during the transition to stationary phase. However, in the absence of glucose, cAMP-CRP second messenger enhances the expression of tnaA as a consequence of cAMP augmentation (Deeley and Yanofsky, 1982). Then, TnaA enzyme converts tryptophan to indole during the transition of exponential to stationary phase (Gaimster and Summers, 2015). It was shown above that YmgC, which is expressed most highly at the onset of stationary phase due to regulation by (p) ppGpp and RpoS (Peano et al., 2015; Traxler et al., 2008), interacts with CysE and inhibits the conversion of serine to O-acetyl serine which is the substrate of CysK to synthesize cysteine. It was contemplated that the deactivation of cysteine biosynthesis by YmgC channels serine flux into tryptophan and (subsequently) indole production, reallocating resources during the onset of stationary phase and allowing rapid accumulation of a crucial quorum sensing molecule. If the hypothesis is correct, phenotypes of the ymgC mutant can be converted via supplementation with indole. Consistently, (Lee et al., 2007a), observed that the addition of indole to the medium reverted the high swarming motility phenotypes of ΔymgC mutant, which was replicated in the strains described herein (FIG. 9), indicating that low indole levels are the reason why the ΔymgC mutant shows high swarming motility compared to WT. Likewise, it was also found that indole has a ~50% stronger effect on biofilm formation in ΔymgC cells compared with WT cells (FIG. 9c-d).

YmgC Overexpression Reduces Biofilm Formation in *Salmonella typhimurium*

Figure 8A:
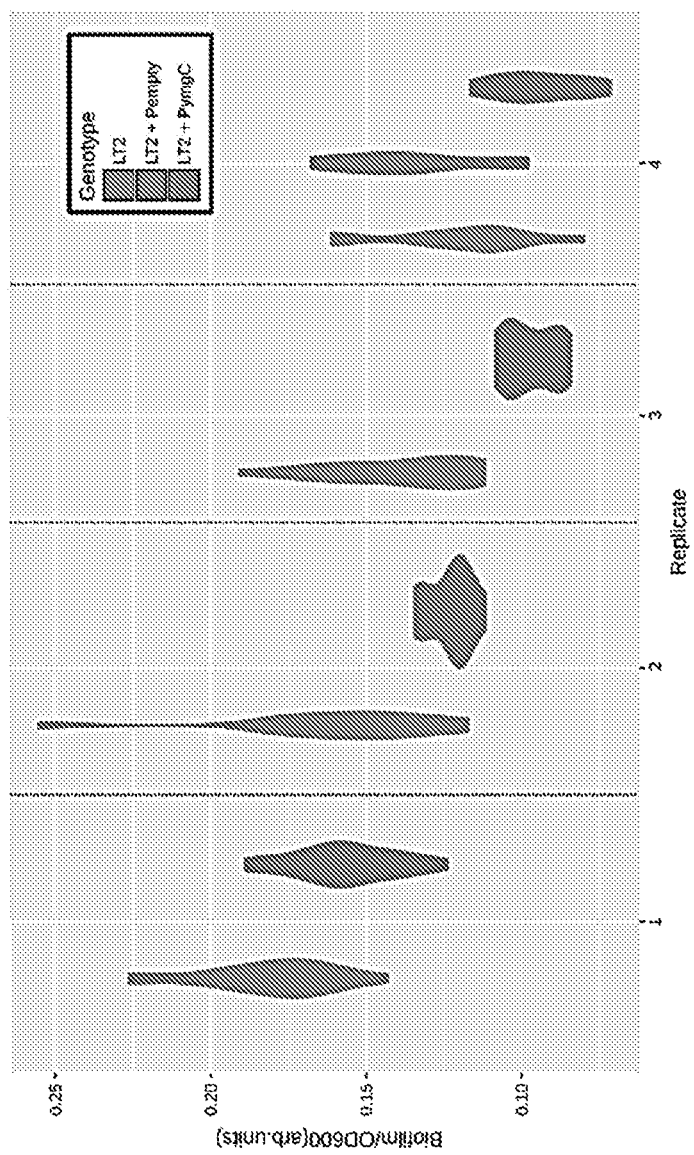

While YmgC itself is unique to *E. coli* and closely related bacteria, and no recognizable homolog exists in *Salmonella* spp., the target enzyme CysE exists and is well conserved across many bacterial genera. It was thus hypothesized that given the conservation of its target, YmgC is able to perform a similar biological function if ectopically expressed in *Salmonella*. Indeed, as shown in FIG. 8, it was observed that overexpression of YmgC in *Salmonella typhimurium* strain LT2 causes a reduction in biofilm formation, consistent with the effects in *E. coli*. These results demonstrate both the generality of biological mechanism employed by YmgC, and the possibility that similar metabolic switches may exist in other bacterial species.

TABLE 1

Summary of bacterial strains and plasmids used in the present study. All KanR based knockouts were transduced from the appropriate Keio collection strains.

| | Description | Source |
|---|---|---|
| Strain | | |
| K-12, W3110 | ATCC 27325 | (Baba et al., 2005) |
| ymgC::kan | BW25113 Complete ymgC replaced by a $Kan^R$ cassette P1 phase transduced into W3110 wildtype | Present study |
| tnaA::kan | BW25113 Complete tnaA replaced by a $Kan^R$ cassette P1 phase transduced into W3110 wildtype | Present study |
| cysE::kan | BW25113 Complete cysE replaced by a $Kan^R$ cassette P1 phase transduced into W3110 wildtype | Present study |
| ΔcysE::ymgC::Kan | ymgC::kan P1 phase transduced in W3110 ΔcysE | Present study |

TABLE 1-continued

Summary of bacterial strains and plasmids used in the present study. All KanR based knockouts were transduced from the appropriate Keio collection strains.

| | Description | Source |
|---|---|---|
| ΔtnaA::ymgC::Kan | ymgC::kan P1 phase transduced in W3110 ΔtnaA | Present study |
| ER2566 | fhuA2 lacZ::T7 gene1 [Ion] ompT gal sulA11 | IMPACT ™ kit |
| | R(mcr-73::miniTn10--TetS)2 [dcm] R(zgb-210::Tn10--Tet(S) | [E6901S, New |
| | endA1 Δ(mcrC-mrr)114::IS10 | England BioLabs] |
| Plasmid | | |
| pCA24NymgC | Plasmid used for overexpression of ymgC, $Cm^R$ | ASKA collection |

Example 2

This Example demonstrates that removing the effects of YmgC had a substantial effect on methionine production. *E. coli* cells (either wild type or ymgC loss of function) were grown to early stationary phase in LB media, and cells were harvested both at the onset of stationary phase and 15 hours later. For harvest, the cells were taken at the given times, centrifuged 5 mins 3000×g at 4° C., then the pellets were mixed with 100 μl PBS, vortexed and centrifuged 3000×g at 4° C. and the supernatants were discarded. Then, the pellets were diluted in 100 μl PBS, mixed, vortexed and then 50 μl of the cells were mixed with 50 μl of 10% trichloroacetic acid and again vortexed and transferred for methionine measurement (see below). The remaining 50 μL of cells was mixed with 50 μl of PBS and sonicated for three bursts of 5 s with a Branson sonifier, centrifuged 5 mins 12000×g, and the supernatants were taken to be used for protein measurement via Bradford assay.

To measure methionine, samples were neutralized and the amino acids were derivatized with o-phthaldialdehyde (OPA) just before injection into an HPLC column. The derivatization was done automatically in an autosampler for each sample before the injection by mixing the sample with OPA reagent and 1 min incubation. This labeling makes amino acid fluorescent derivatives with excitation at 340 nm and emission at 450 nm. The derivatized samples were analyzed using C18 HPLC column using acetate buffer with methanol gradient and fluorescent detection of amino acid peaks. Methionine calibration solution was used for quantification of the data. The reported data are then methionine levels normalized by protein content.

Figure 10A:
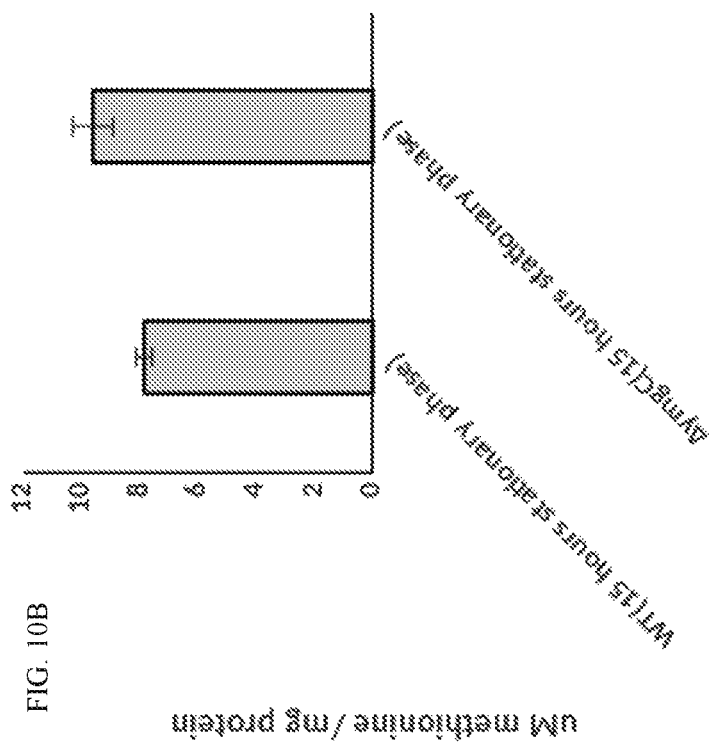
FIG. 10A through FIG. 10B shows measurements of intracellular methionine in normal cells or cells with ymgC deleted, either at the end of exponential phase or while in stationary phase.
Figure 10B:
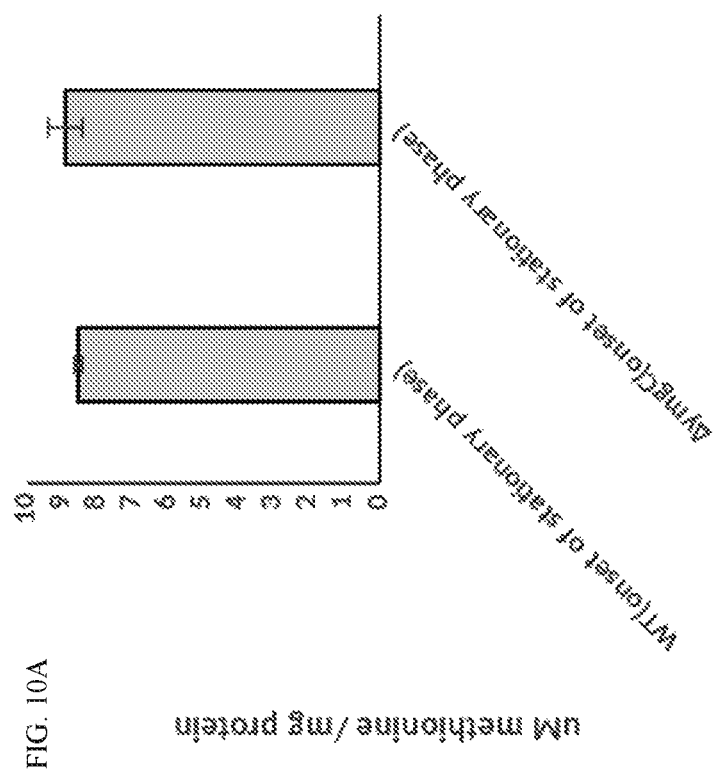

Results are shown in FIG. 10. FIG. 10 shows intracellular methionine in either normal cells or cells with ymgC deleted, either at the end of exponential phase or while in stationary phase. Removal of ymgC leads to a substantial increase (~20%) in methionine levels during stationary phase, which is an industrially relevant timepoint.

Example 3

Experiments are conducted to assay methionine and cysteine production in *E. coli* knockout or overexpression strains using the methods described in Examples 1 and 2 above. Strains lacking one or more of the following genes are prepared: poxB, glgC, ymgC, tnaA, pgaC, yaiP, ugD, ptA, ldhA, ashe, or pflB. In addition, strains that overexpress metH and/or yjeH are prepared. In some embodiments, strains have a cysE (M256->R) mutation that removes feedback inhibition of this enzyme. It is contemplated that these strains will exhibit increased production of methionine and/or cysteine relative to wild type *E. coli*.

REFERENCES

Awano, N., Wada, M., Kohdoh, A., Oikawa, T., Takagi, H., and Nakamori, S. (2003). Effect of cysteine desulfhydrase gene disruption on L-cysteine overproduction in *Escherichia coli*. Appl. Microbiol. Biotechnol. 62, 239-243.

Awano, N., Wada, M., Mori, H., Nakamori, S., and Takagi, H. (2005). Identification and functional analysis of *Escherichia coli* cysteine desulfhydrases. Appl. Environ. Microbiol. 71, 4149-4152.

Baba, T., Ara, T., Hasegawa, M., Takai, Y., Okumura, Y., Baba, M., Datsenko, K. A., Tomita, M., Wanner, B. L., and Mori, H. (2006). Construction of *Escherichia coli* K-12 in-frame, single-gene knockout mutants: the Keio collection. Mol. Syst. Biol. 2, 2006.0008.

Bansal, T., Englert, D., Lee, J., Hegde, M., Wood, T. K., and Jayaraman, A. (2007). Differential effects of epinephrine, norepinephrine, and indole on *Escherichia coli* O157:H7 chemotaxis, colonization, and gene expression. Infect. Immun. 75, 4597-4607.

Bates, D., Mächler, M., Bolker, B., and Walker, S. (2015). Fitting Linear Mixed-Effects Models Using lme4. Journal of Statistical Software, Articles 67, 1-48.

Bergholz, T. M., Wick, L. M., Qi, W., Riordan, J. T., Ouellette, L. M., and Whittam, T. S. (2007). Global transcriptional response of *Escherichia coli* O157: H7 to growth transitions in glucose minimal medium. BMC Microbiol. 7, 97.

Bourassa, L., and Camilli, A. (2009). Glycogen contributes to the environmental persistence and transmission of *Vibrio cholerae*. Mol. Microbiol. 72, 124-138.

Bürkner, P.-C. (2017). brms: An R Package for Bayesian Multilevel Models Using Stan. Journal of Statistical Software, Articles 80, 1-28.

Butler, M. T., Wang, Q., and Harshey, R. M. (2010). Cell density and mobility protect swarming bacteria against antibiotics. Proc. Natl. Acad. Sci. U.S.A. 107, 3776-3781.

Chang, D.-E., Smalley, D. J., Tucker, D. L., Leatham, M. P., Norris, W. E., Stevenson, S. J., Anderson, A. B., Grissom, J. E., Laux, D. C., Cohen, P. S., et al. (2004). Carbon nutrition of *Escherichia coli* in the mouse intestine. Proc. Natl. Acad. Sci. U.S.A. 101, 7427-7432.

Croxen, M. A., Law, R. J., Scholz, R., Keeney, K. M., Wlodarska, M., and Finlay, B. B. (2013). Recent advances in understanding enteric pathogenic *Escherichia coli*. Clin. Microbiol. Rev. 26, 822-880.

Datsenko, K. A., and Wanner, B. L. (2000). One-step inactivation of chromosomal genes in *Escherichia coli* K-12 using PCR products. Proc. Natl. Acad. Sci. U.S.A. 97, 6640-6645.

Deeley, M. C., and Yanofsky, C. (1982). Transcription initiation at the tryptophanase promoter of *Escherichia coli* K-12. J. Bacteriol. 151, 942-951.

Durfee, T., Hansen, A.-M., Zhi, H., Blattner, F. R., and Jin, D. J. (2008). Transcription profiling of the stringent response in *Escherichia coli*. J. Bacteriol. 190, 1084-1096.

van Elsas, J. D., Semenov, A. V., Costa, R., and Trevors, J. T. (2011). Survival of *Escherichia coli* in the environment: fundamental and public health aspects. ISME J. 5, 173-183.

Eydallin, G., Viale, A. M., Morán-Zorzano, M. T., Muñoz, F. J., Montero, M., Baroja-Fernández, E., and Pozueta-Romero, J. (2007). Genome-wide screening of genes affecting glycogen metabolism in *Escherichia coli* K-12. FEBS Lett. 581, 2947-2953.

Eydallin, G., Montero, M., Almagro, G., Sesma, M. T., Viale, A. M., Muñoz, F. J., Rahimpour, M., Baroja-Fernández, E., and Pozueta-Romero, J. (2010). Genome-wide screening of genes whose enhanced expression affects glycogen accumulation in *Escherichia coli*. DNA Res. 17, 61-71.

Ferla, M. P., and Patrick, W. M. (2014). Bacterial methionine biosynthesis. Microbiology 160, 1571-1584.

Gaimster, H., and Summers, D. (2015). Regulation of Indole Signalling during the Transition of *E. coli* from Exponential to Stationary Phase. PLOS One 10, e0136691.

Garavaglia, M., Rossi, E., and Landini, P. (2012). The pyrimidine nucleotide biosynthetic pathway modulates production of biofilm determinants in *Escherichia coli*. PLOS One 7, e31252.

Garges, S. (1993). A Short Course in Bacterial Genetics. A Laboratory Manual and Handbook for *Escherichia coli* and Related Bacteria. By Jeffrey H. Miller. Cold Spring Harbor Laboratory, Cold Spring Harbor, New York, 1992. Anal. Biochem. 210, 217. Gentry, D. R., Hernandez, V. J., Nguyen, L. H., Jensen, D. B., and Cashel, M. (1993). Synthesis of the stationary-phase sigma factor sigma s is positively regulated by ppGpp. J. Bacteriol. 175, 7982-7989.

Hirakawa, H., Inazumi, Y., Masaki, T., Hirata, T., and Yamaguchi, A. (2005). Indole induces the expression of multidrug exporter genes in *Escherichia coli*. Mol. Microbiol. 55, 1113-1126.

Hol, F. J. H., Hubert, B., Dekker, C., and Keymer, J. E. (2016). Density-dependent adaptive resistance allows swimming bacteria to colonize an antibiotic gradient. ISME J. 10, 30-38.

Jones, S. A., Jorgensen, M., Chowdhury, F. Z., Rodgers, R., Hartline, J., Leatham, M. P., Struve, C., Krogfelt, K. A., Cohen, P. S., and Conway, T. (2008). Glycogen and maltose utilization by *Escherichia coli* O157: H7 in the mouse intestine. Infect. Immun. 76, 2531-2540.

Kanjee, U., and Houry, W. A. (2013). Mechanisms of acid resistance in *Escherichia coli*. Annu. Rev. Microbiol. 67, 65-81.

Kannan, G., Wilks, J. C., Fitzgerald, D. M., Jones, B. D., Bondurant, S. S., and Slonczewski, J. L. (2008). Rapid acid treatment of *Escherichia coli*: transcriptomic response and recovery. BMC Microbiol. 8, 37.

Kitagawa, M., Ara, T., Arifuzzaman, M., Ioka-Nakamichi, T., Inamoto, E., Toyonaga, H., and Mori, H. (2005). Complete set of ORF clones of *Escherichia coli* ASKA library (a complete set of *E. coli* K-12 ORF archive): unique resources for biological research. DNA Res. 12, 291-299.

Kumar, S., Raj, I., Nagpal, I., Subbarao, N., and Gourinath, S. (2011). Structural and biochemical studies of serine acetyltransferase reveal why the parasite *Entamoeba histolytica* cannot form a cysteine synthase complex. J. Biol. Chem. 286, 12533-12541.

Lane, M. C., Lockatell, V., Monterosso, G., Lamphier, D., Weinert, J., Hebel, J. R., Johnson, D. E., and Mobley, H. L. T. (2005). Role of motility in the colonization of uropathogenic *Escherichia coli* in the urinary tract. Infect. Immun. 73, 7644-7656.

Lee, J.-H., and Lee, J. (2010). Indole as an intercellular signal in microbial communities. FEMS Microbiol. Rev. 34, 426-444.

Lee, H. H., Molla, M. N., Cantor, C. R., and Collins, J. J. (2010). Bacterial charity work leads to population-wide resistance. Nature 467, 82-85.

Lee, J., Page, R., García-Contreras, R., Palermino, J.-M., Zhang, X.-S., Doshi, O., Wood, T. K., and Peti, W. (2007a). Structure and function of the *Escherichia coli* protein YmgB: a protein critical for biofilm formation and acid-resistance. J. Mol. Biol. 373, 11-26.

Lee, J., Jayaraman, A., and Wood, T. K. (2007b). Indole is an inter-species biofilm signal mediated by SdiA. BMC Microbiol. 7, 42.

Lee, J., Zhang, X.-S., Hegde, M., Bentley, W. E., Jayaraman, A., and Wood, T. K. (2008). Indole cell signaling occurs primarily at low temperatures in *Escherichia coli*. ISME J. 2, 1007-1023.

Lehnen, D., Blumer, C., Polen, T., Wackwitz, B., Wendisch, V. F., and Unden, G. (2002). LrhA as a new transcriptional key regulator of flagella, motility and chemotaxis genes in *Escherichia coli*. Mol. Microbiol. 45, 521-532.

Lemke, J. J., Durfee, T., and Gourse, R. L. (2009). DksA and ppGpp directly regulate transcription of the *Escherichia coli* flagellar cascade. Mol. Microbiol. 74, 1368-1379.

Li, G., and Young, K. D. (2013). Indole production by the tryptophanase TnaA in *Escherichia coli* is determined by the amount of exogenous tryptophan. Microbiology 159, 402-410.

Li, G., and Young, K. D. (2014). A cAMP-independent carbohydrate-driven mechanism inhibits tnaA expression and TnaA enzyme activity in *Escherichia coli*. Microbiology 160, 2079-2088.

McMeechan, A., Lovell, M. A., Cogan, T. A., Marston, K. L., Humphrey, T. J., and Barrow, P. A. (2005). Glycogen production by different *Salmonella enterica* serotypes: contribution of functional glgC to virulence, intestinal colonization and environmental survival. Microbiology 151, 3969-3977.

Montero, M., Eydallin, G., Viale, A. M., Almagro, G., Muñoz, F. J., Rahimpour, M., Sesma, M. T., Baroja-Fernández, E., and Pozueta-Romero, J. (2009). *Escherichia coli* glycogen metabolism is controlled by the PhoP-PhoQ regulatory system at submillimolar environmental Mg2+ concentrations, and is highly interconnected with a wide variety of cellular processes. Biochem. J 424, 129-141.

Mundhada, H., Schneider, K., Christensen, H. B., and Nielsen, A. T. (2016). Engineering of high yield production of L-serine in *Escherichia coli*. Biotechnol. Bioeng. 113, 807-816.

Newton, W. A., Morino, Y., and Snell, E. E. (1965). PROPERTIES OF CRYSTALLINE TRYPTOPHANASE. J. Biol. Chem. 240, 1211-1218.

Nichols, R. J., Sen, S., Choo, Y. J., Beltrao, P., Zietek, M., Chaba, R., Lee, S., Kazmierczak, K. M., Lee, K. J., Wong, A., et al. (2011). Phenotypic landscape of a bacterial cell. Cell 144, 143-156.

Niu, C., Graves, J. D., Mokuolu, F. O., Gilbert, S. E., and Gilbert, E. S. (2005). Enhanced swarming of bacteria on agar plates containing the surfactant Tween 80. J. Microbiol. Methods 62, 129-132.

O'Toole, G. A., and Kolter, R. (1998). Initiation of biofilm formation in *Pseudomonas fluorescens* WCS365 proceeds via multiple, convergent signalling pathways: a genetic analysis. Mol. Microbiol. 28, 449-461.

Palevsky, N., Shemer, B., Connolly, J. P. R., and Belkin, S. (2016). The Highly Conserved *Escherichia coli* Transcription Factor YhaJ Regulates Aromatic Compound Degradation. Front. Microbiol. 7, 1490.

Patten, C. L., Kirchhof, M. G., Schertzberg, M. R., Morton, R. A., and Schellhorn, H. E. (2004). Microarray analysis of RpoS-mediated gene expression in *Escherichia coli* K-12. Mol. Genet. Genomics 272, 580-591.

Peano, C., Wolf, J., Demol, J., Rossi, E., Petiti, L., De *Bellis*, G., Geiselmann, J., Egli, T., Lacour, S., and Landini, P. (2015). Characterization of the *Escherichia coli* o(S) core regulon by Chromatin Immunoprecipitation-sequencing (ChIP-seq) analysis. Sci. Rep. 5, 10469.

Pizer, L. I. (1963). THE PATHWAY AND CONTROL OF SERINE BIOSYNTHESIS IN *ESCHERICHIA COLI*. J. Biol. Chem. 238, 3934-3944.

Plummer-Proceedings of the 3rd international workshop on, M., and 2003 (2003). JAGS: A program for analysis of Bayesian graphical models using Gibbs sampling.

Potrykus, K., and Cashel, M. (2008). (p) ppGpp: still magical? Annu. Rev. Microbiol. 62, 35-51.

Pratt, L. A., and Kolter, R. (1998). Genetic analysis of *Escherichia coli* biofilm formation: roles of flagella, motility, chemotaxis and type I pili. Mol. Microbiol. 30, 285-293.

Pye, V. E., Tingey, A. P., Robson, R. L., and Moody, P. C. E. (2004). The structure and mechanism of serine acetyltransferase from *Escherichia coli*. J. Biol. Chem. 279, 40729-40736.

Raboni, S., Bettati, S., and Mozzarelli, A. (2009). Tryptophan synthase: a mine for enzymologists. Cell. Mol. Life Sci. 66, 2391-2403.

Rahimpour, M., Montero, M., Almagro, G., Viale, A. M., Sevilla, Á., Cánovas, M., Muñoz, F. J., Baroja-Fernández, E., Bahaji, A., Eydallin, G., et al. (2013). GlgS, described previously as a glycogen synthesis control protein, negatively regulates motility and biofilm formation in *Escherichia coli*. Biochem. J 452, 559-573.

Rahman, M., Hasan, M. R., Oba, T., and Shimizu, K. (2006). Effect of rpoS gene knockout on the metabolism of *Escherichia coli* during exponential growth phase and early stationary phase based on gene expressions, enzyme activities and intracellular metabolite concentrations. Biotechnol. Bioeng. 94, 585-595.

Riddles, P. W., Blakeley, R. L., and Zerner, B. (1983). [8] Reassessment of Ellman's reagent. In Enzyme Structure Part I, (Elsevier), pp. 49-60.

Roy, A., Yang, J., and Zhang, Y. (2012). COFACTOR: an accurate comparative algorithm for structure-based protein function annotation. Nucleic Acids Res. 40, W471-W477.

Saito, K., Yokoyama, H., Noji, M., and Murakoshi, I. (1995). Molecular cloning and characterization of a plant serine acetyltransferase playing a regulatory role in cysteine biosynthesis from watermelon. J. Biol. Chem. 270, 16321-16326.

Sambou, T., Dinadayala, P., Stadthagen, G., Barilone, N., Bordat, Y., Constant, P., Levillain, F., Neyrolles, O., Gicquel, B., Lemassu, A., et al. (2008). Capsular glucan and intracellular glycogen of *Mycobacterium tuberculosis*: biosynthesis and impact on the persistence in mice. Mol. Microbiol. 70, 762-774.

Sharma, G., Sharma, S., Sharma, P., Chandola, D., Dang, S., Gupta, S., and Gabrani, R. (2016). *Escherichia coli* biofilm: development and therapeutic strategies. J. Appl. Microbiol. 121, 309-319.

Sievers, F., Wilm, A., Dineen, D., Gibson, T. J., Karplus, K., Li, W., Lopez, R., McWilliam, H., Remmert, M., Söding, J., et al. (2011). Fast, scalable generation of high-quality protein multiple sequence alignments using Clustal Omega. Mol. Syst. Biol. 7, 539. Singh, P., Brooks, J. F., 2nd, Ray, V. A., Mandel, M. J., and Visick, K. L. (2015). CysK Plays a Role in Biofilm Formation and Colonization by *Vibrio fischeri*. Appl. Environ. Microbiol. 81, 5223-5234.

Snell, E. E. (1975). Tryptophanase: structure, catalytic activities, and mechanism of action. Adv. Enzymol. Relat. Areas Mol. Biol. 42, 287-333.

Snell, E. E. (2006). Tryptophanase: Structure, Catalytic Activities, and Mechanism of Action: Meister/Advances. In Advances in Enzymology and Related Areas of Molecular Biology, A. Meister, ed. (Hoboken, NJ, USA: John Wiley & Sons, Inc.), pp. 287-333.

Srivatsan, A., and Wang, J. D. (2008). Control of bacterial transcription, translation and replication by (p) ppGpp. Curr. Opin. Microbiol. 11, 100-105.

Stouthamer, A. H. (1973). A theoretical study on the amount of ATP required for synthesis of microbial cell material. Antonie Van Leeuwenhoek 39, 545-565. Terashima, H., Kojima, S., and Homma, M. (2008). Chapter 2 Flagellar Motility in Bacteria. (Elsevier), pp. 39-85.

Traxler, M. F., Summers, S. M., Nguyen, H.-T., Zacharia, V. M., Hightower, G. A., Smith, J. T., and Conway, T. (2008). The global, ppGpp-mediated stringent response to amino acid starvation in *Escherichia coli*. Mol. Microbiol. 68, 1128-1148.

Verstraeten, N., Braeken, K., Debkumari, B., Fauvart, M., Fransaer, J., Vermant, J., and Michiels, J. (2008). Living on a surface: swarming and biofilm formation. Trends Microbiol. 16, 496-506.

Wang, L., and Wise, M. J. (2011). Glycogen with short average chain length enhances bacterial durability. Naturwissenschaften 98, 719-729.

Whitfield, C. (2006). Biosynthesis and assembly of capsular polysaccharides in *Escherichia coli*. Annu. Rev. Biochem. 75, 39-68.

Wickham, H. (2016). ggplot2: Elegant Graphics for Data Analysis (Springer).

Wood, T. K., González Barrios, A. F., Herzberg, M., and Lee, J. (2006). Motility influences biofilm architecture in *Escherichia coli*. Appl. Microbiol. Biotechnol. 72, 361-367.

Xu, D., and Zhang, Y. (2012). Ab initio protein structure assembly using continuous structure fragments and optimized knowledge-based force field. Proteins 80, 1715-1735.

Yamamotoya, T., Dose, H., Tian, Z., Fauré, A., Toya, Y., Honma, M., Igarashi, K., Nakahigashi, K., Soga, T., Mori, H., et al. (2012). Glycogen is the primary source of glucose during the lag phase of *E. coli* proliferation. Biochim. Biophys. Acta 1824, 1442-1448.

Zhang, C., Freddolino, P. L., and Zhang, Y. (2017). COFACTOR: improved protein function prediction by combining structure, sequence and protein-protein interaction information. Nucleic Acids Res.

Zhang, X.-S., García-Contreras, R., and Wood, T. K. (2008). *Escherichia coli* transcription factor YncC (McbR) regulates colanic acid and biofilm formation by repressing expression of periplasmic protein YbiM (McbA). ISME J. 2, 615-631.

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

The invention claimed is:

1. A method of killing or inhibiting growth of bacteria in a biofilm, comprising:
    contacting bacteria in a biofilm with a composition comprising an *E. coli* ymgC polypeptide having the sequence of SEQ ID NO: 1, wherein said contacting kills or inhibits the growth of said bacteria.

2. The method of claim 1, wherein said biofilm is on a surface of an object.

3. The method of claim 2, wherein said object is a medical device.

4. The method of claim 1, wherein said biofilm is in or on a subject.

5. The method of claim 4, wherein said biofilm is in a wound.

6. The method of claim 1, wherein said ymgC polypeptide is formulated as a pharmaceutical composition, a disinfecting, a cleaning solution, or is on a wound dressing.

* * * * *

UNITED STATES PATENT AND TRADEMARK OFFICE
CERTIFICATE OF CORRECTION

| | | |
|---|---|---|
| PATENT NO. | : 12,246,056 B2 | Page 1 of 1 |
| APPLICATION NO. | : 17/291812 | |
| DATED | : March 11, 2025 | |
| INVENTOR(S) | : Freddolino et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 705 days.

Signed and Sealed this
Sixth Day of January, 2026

John A. Squires
*Director of the United States Patent and Trademark Office*

SEQUENCE LISTING

```
<160> NUMBER OF SEQ ID NOS: 1

<210> SEQ ID NO 1
<211> LENGTH: 82
<212> TYPE: PRT
<213> ORGANISM: Artificial Sequence
<220> FEATURE:
<223> OTHER INFORMATION: Synthetic Construct

<400> SEQUENCE: 1

Met Asn Asn Ser Ile Pro Glu Arg Phe Ile Phe Gln Cys Ala Leu Phe
1               5                   10                  15

Lys Asn Leu Glu Arg Glu Val Phe Met Thr His Gly Tyr Val Asp Ser
            20                  25                  30

His Ile Ile Asp Gln Ala Leu Arg Leu Arg Leu Lys Asp Glu Thr Ser
        35                  40                  45

Val Ile Leu Ser Asp Leu Tyr Leu Gln Ile Leu Gln Tyr Ile Glu Met
    50                  55                  60

His Lys Thr Thr Leu Thr Asp Ile Ile Ile Asn Asp Arg Glu Ser Val
65                  70                  75                  80

Leu Ser
```